United States Patent [19]
Haas

[11] Patent Number: 6,109,776
[45] Date of Patent: Aug. 29, 2000

[54] METHOD AND SYSTEM FOR COMPUTATIONALLY IDENTIFYING CLUSTERS WITHIN A SET OF SEQUENCES

[75] Inventor: Juergen Haas, Gaithersburg, Md.

[73] Assignee: Gene Logic, Inc., Gaithersburg, Md.

[21] Appl. No.: 09/063,450

[22] Filed: Apr. 21, 1998

[51] Int. Cl.[7] .............................. G01N 1/00; G01N 31/00; C12Q 1/68; G06G 7/48
[52] U.S. Cl. .............................. 364/496; 435/6; 364/497; 364/578; 702/127; 702/30
[58] Field of Search ...................... 364/496, 497, 364/578; 435/6; 702/127, 30

[56] References Cited

U.S. PATENT DOCUMENTS 5,867,402  2/1999  Schneider et al. ...................... 364/496

OTHER PUBLICATIONS

Schneider et al NAR vol. 18 No. 20 pp.6097–6100, 1990.
Mehldau et al CABIOS vol. 9, No. 3 pp. 299–314, 1993.
Pesole et al NAR vol. 20, No. 11 pp. 2871–2875, 1992.
Lefevre et al CABIOS vol. 9, No. 3 pp. 349–354, 1993.
Staden NAR vol. 12, No. 1 pp. 505–519, 1984.

Primary Examiner—Kenneth R. Horlick
Assistant Examiner—Jeffrey Siew
Attorney, Agent, or Firm—Weiss Jensen Ellis & Howard

[57] ABSTRACT

A method and system for computationally analyzing an initial set of patterns in order to identify subsets of patterns, called clusters, that contain common sub-patterns. The patterns of the initial set of patterns are represented as linear sequences of subunits, and the common sub-patterns occur as sub-sequences of subunits within the linear sequences starting at different positions within the different linear sequences. Variations in the offset and in the sequence of subunits within a common sub-pattern are considered in the analysis. In one embodiment, an initial set of oligonucleotide sequences that are produced by various biochemical techniques are computationally analyzed to identify clusters that may correspond to a number of different binding sites for DNA-binding proteins within one or more double-stranded DNA duplexes. The method places each oligonucleotide sequence within a new cluster and calculates an initial information weight matrix for that cluster. Then, other sequences from the initial set of sequences are added to the cluster and the information weight matrix of the cluster is re-computed until the information content of the information weight matrix falls below a threshold value.

41 Claims, 15 Drawing Sheets

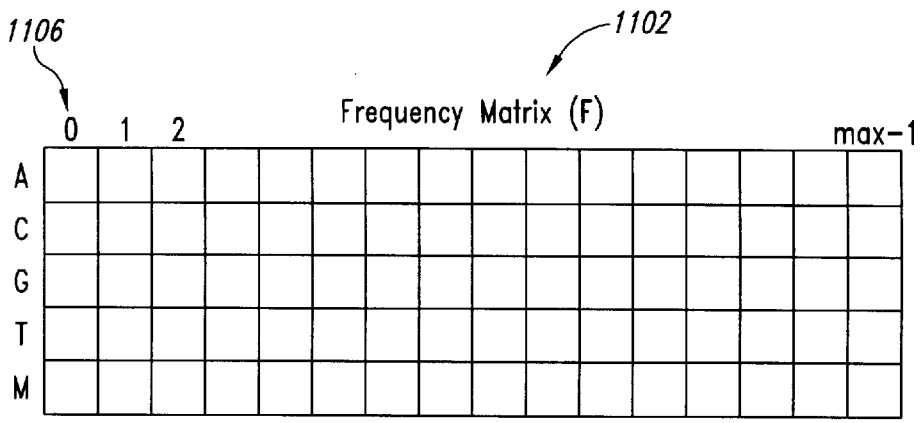
Fig. 11A
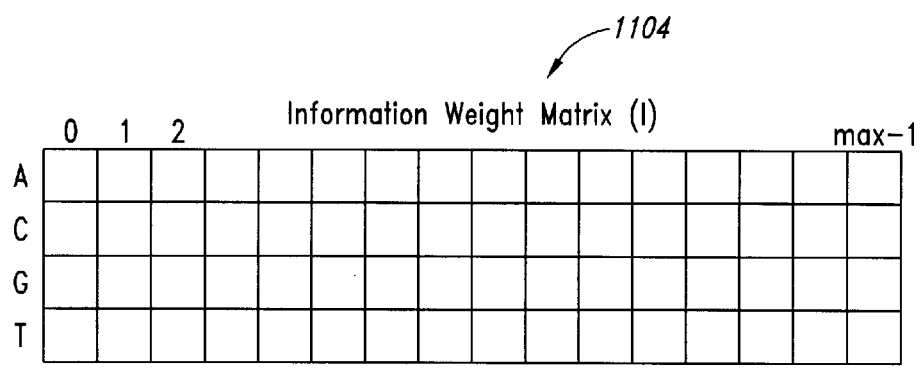
Fig. 11B
1 CATACAATGC ← 1202
2 CCCCCCCCCC
3 CTTGGATAA
4 GTGGGGTAA
5 ACACAATGCG
6 CAGTTCTAGG
7 AAGGAGGCAG
8 ACACGATGCG
9 TCCATGTATT
10 GTGTATGAGC
11 CGCGGATATG
12 AACTATGATC
13 TCATTGTGAG
14 GGATTTAGCT
15 CGTGGGAACT
Fig. 12

Cluster size: 1  1303  ⟵1301
Sequence 1: MMMCATACAATGC

Fig. 13A

Frequency Matrix:    ⟵1304

|   | 0 | 1 | 2 | 3 | 4 | 5 | 6 | 7 | 8 | 9 | 10 | 11 | 12 | 13 | 14 | 15 |
|---|---|---|---|---|---|---|---|---|---|---|----|----|----|----|----|----|
| A | 0.0 | 0.0 | 0.0 | 0.0 | 1.0 | 0.0 | 1.0 | 0.0 | 1.0 | 1.0 | 0.0 | 0.0 | 0.0 | 0.0 | 0.0 | 0.0 |
| C | 0.0 | 0.0 | 0.0 | 1.0 | 0.0 | 0.0 | 0.0 | 1.0 | 0.0 | 0.0 | 0.0 | 0.0 | 1.0 | 0.0 | 0.0 | 0.0 |
| G | 0.0 | 0.0 | 0.0 | 0.0 | 0.0 | 0.0 | 0.0 | 0.0 | 0.0 | 0.0 | 0.0 | 1.0 | 0.0 | 0.0 | 0.0 | 0.0 |
| T | 0.0 | 0.0 | 0.0 | 0.0 | 0.0 | 1.0 | 0.0 | 0.0 | 0.0 | 0.0 | 1.0 | 0.0 | 0.0 | 0.0 | 0.0 | 0.0 |
| M | 1.0 | 1.0 | 1.0 | 0.0 | 0.0 | 0.0 | 0.0 | 0.0 | 0.0 | 0.0 | 0.0 | 0.0 | 0.0 | 1.0 | 1.0 | 1.0 |

Fig. 13B

Information weight matrix

|   | 0 | 1 | 2 | 3 | 4 | 5 | 6 | 7 | 8 | 9 | 10 | 11 | 12 | 13 | 14 | 15 |
|---|---|---|---|---|---|---|---|---|---|---|----|----|----|----|----|----|
| A | 0.0 | 0.0 | 0.0 | -14. | 2.0 | -14. | 2.0 | -14. | 2.0 | 2.0 | -14. | -14. | -14. | 0.0 | 0.0 | 0.0 |
| C | 0.0 | 0.0 | 0.0 | 2.0 | -14. | -14. | -14. | 2.0 | -14. | -14. | -14. | -14. | 2.0 | 0.0 | 0.0 | 0.0 |
| G | 0.0 | 0.0 | 0.0 | -14. | -14. | -14. | -14. | -14. | -14. | -14. | -14. | 2.0 | -14. | 0.0 | 0.0 | 0.0 |
| T | 0.0 | 0.0 | 0.0 | -14. | -14. | 2.0 | -14. | -14. | -14. | -14. | 2.0 | -14. | -14. | 0.0 | 0.0 | 0.0 |

Fig. 13C

Cluster size: 2  1403  1402
Sequence 1: MMMCATACAATGC
Sequence 5: MMMMACACAATGCG
1404  1401

*Fig. 14A*

Frequency Matrix:
|   | 0 | 1 | 2 | 3 | 4 | 5 | 6 | 7 | 8 | 9 | 10 | 11 | 12 | 13 | 14 | 15 |
|---|---|---|---|---|---|---|---|---|---|---|----|----|----|----|----|----|
| A | 0.0 | 0.0 | 0.0 | 0.0 | 1.0 | 0.0 | 1.0 | 0.0 | 1.0 | 1.0 | 0.0 | 0.0 | 0.0 | 0.0 | 0.0 | 0.0 |
| C | 0.0 | 0.0 | 0.0 | 0.5 | 0.0 | 0.5 | 0.0 | 1.0 | 0.0 | 0.0 | 0.0 | 0.0 | 1.0 | 0.0 | 0.0 | 0.0 |
| G | 0.0 | 0.0 | 0.0 | 0.0 | 0.0 | 0.0 | 0.0 | 0.0 | 0.0 | 0.0 | 0.0 | 1.0 | 0.0 | 0.5 | 0.0 | 0.0 |
| T | 0.0 | 0.0 | 0.0 | 0.0 | 0.0 | 0.5 | 0.0 | 0.0 | 0.0 | 0.0 | 1.0 | 0.0 | 0.0 | 0.0 | 0.0 | 0.0 |
| M | 1.0 | 1.0 | 1.0 | 0.5 | 0.0 | 0.0 | 0.0 | 0.0 | 0.0 | 0.0 | 0.0 | 0.0 | 0.0 | 0.5 | 1.0 | 1.0 |

*Fig. 14B*

Information weight matrix
|   | 0 | 1 | 2 | 3 | 4 | 5 | 6 | 7 | 8 | 9 | 10 | 11 | 12 | 13 | 14 | 15 |
|---|---|---|---|---|---|---|---|---|---|---|----|----|----|----|----|----|
| A | 0.0 | 0.0 | 0.0 | -1.0 | 2.0 | -14. | 2.0 | -14. | 2.0 | 2.0 | -14. | -14. | -14. | -1.0 | 0.0 | 0.0 |
| C | 0.0 | 0.0 | 0.0 | 1.32 | -14. | 1.0 | -14. | 2.0 | -14. | -14. | -14. | -14. | 2.0 | -1.0 | 0.0 | 0.0 |
| G | 0.0 | 0.0 | 0.0 | -1.0 | -14. | -14. | -14. | -14. | -14. | -14. | -14. | 2.0 | -14. | 1.32 | 0.0 | 0.0 |
| T | 0.0 | 0.0 | 0.0 | -1.0 | -14. | 1.0 | -14. | -14. | -14. | -14. | 2.0 | -14. | -14. | -1.0 | 0.0 | 0.0 |

*Fig. 14C*

Cluster size: 3
Sequence 1: MMMCATACAATGC
Sequence 5: MMMMACACAATGCG
Sequence 8: MMMMACACGATGCG

*Fig. 15A*

Frequency Matrix:

|   | 0 | 1 | 2 | 3 | 4 | 5 | 6 | 7 | 8 | 9 | 10 | 11 | 12 | 13 | 14 | 15 |
|---|---|---|---|---|---|---|---|---|---|---|----|----|----|----|----|----|
| A | 0.0 | 0.0 | 0.0 | 0.0 | 1.0 | 0.0 | 1.0 | 0.0 | 0.66 | 1.0 | 0.0 | 0.0 | 0.0 | 0.0 | 0.0 | 0.0 |
| C | 0.0 | 0.0 | 0.0 | 0.33 | 0.0 | 0.66 | 0.0 | 1.0 | 0.0 | 0.0 | 0.0 | 0.0 | 1.0 | 0.0 | 0.0 | 0.0 |
| G | 0.0 | 0.0 | 0.0 | 0.0 | 0.0 | 0.0 | 0.0 | 0.0 | 0.33 | 0.0 | 0.0 | 1.0 | 0.0 | 0.66 | 0.0 | 0.0 |
| T | 0.0 | 0.0 | 0.0 | 0.0 | 0.0 | 0.33 | 0.0 | 0.0 | 0.0 | 0.0 | 1.0 | 0.0 | 0.0 | 0.0 | 0.0 | 0.0 |
| M | 1.0 | 1.0 | 1.0 | 0.66 | 0.0 | 0.0 | 0.0 | 0.0 | 0.0 | 0.0 | 0.0 | 0.0 | 0.0 | 0.33 | 1.0 | 1.0 |

*Fig. 15B*

Information weight matrix

|   | 0 | 1 | 2 | 3 | 4 | 5 | 6 | 7 | 8 | 9 | 10 | 11 | 12 | 13 | 14 | 15 |
|---|---|---|---|---|---|---|---|---|---|---|----|----|----|----|----|----|
| A | 0.0 | 0.0 | 0.0 | -0.5 | 2.0 | -14. | 2.0 | -14. | 1.41 | 2.0 | -14. | -14. | -14. | -1.5 | 0.0 | 0.0 |
| C | 0.0 | 0.0 | 0.0 | 1.0 | -14. | 1.41 | -14. | 2.0 | -14. | -14. | -14. | -14. | 2.0 | -1.5 | 0.0 | 0.0 |
| G | 0.0 | 0.0 | 0.0 | -0.5 | -14. | -14. | -14. | -14. | 0.41 | -14. | -14. | 2.0 | -14. | 1.58 | 0.0 | 0.0 |
| T | 0.0 | 0.0 | 0.0 | -0.5 | -14. | 0.41 | -14. | -14. | -14. | -14. | 2.0 | -14. | -14. | -1.5 | 0.0 | 0.0 |

*Fig. 15C*

SEQUENCE LISTING

```
<160> NUMBER OF SEQ ID NOS: 38

<210> SEQ ID NO 1
<211> LENGTH: 9
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 1 ccgtttacc                                                              9

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 2
aaaagggggg                                                            10

<210> SEQ ID NO 3
<211> LENGTH: 7
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 3 ggaaggc                                                                7

<210> SEQ ID NO 4
<211> LENGTH: 8
<212> TYPE: DNA
<213> ORGANISM: Artificial Sequence
<220> FEATURE:
```

```
<223> OTHER INFORMATION: Description of Artificial Sequence:example
      sequence illustrating a computational methodology

<400> SEQUENCE: 4 tctctgtc                                                                    8

<210> SEQ ID NO 5
<211> LENGTH: 8
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 5 aaatccga                                                                    8

<210> SEQ ID NO 6
<211> LENGTH: 8
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 6 gtctaccg                                                                    8

<210> SEQ ID NO 7
<211> LENGTH: 9
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 7 cggatggca                                                                   9

<210> SEQ ID NO 8
<211> LENGTH: 8
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 8 aatcccta                                                                    8

<210> SEQ ID NO 9
<211> LENGTH: 9
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 9 tatcgctag                                                                   9

<210> SEQ ID NO 10
<211> LENGTH: 9
<212> TYPE: DNA
<213> ORGANISM: Artificial Sequence
<220> FEATURE:
<223> OTHER INFORMATION: Description of Artificial Sequence:example
``` sequence illustrating a computational methodology

<400> SEQUENCE: 10 gggaaggtg                                                                          9

<210> SEQ ID NO 11
<211> LENGTH: 9
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 11 ctgtttacc                                                                          9

<210> SEQ ID NO 12
<211> LENGTH: 8
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 12 agggaagc                                                                           8

<210> SEQ ID NO 13
<211> LENGTH: 8
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 13 atcgttcc                                                                           8

<210> SEQ ID NO 14
<211> LENGTH: 8
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 14 tatccgaa                                                                           8

<210> SEQ ID NO 15
<211> LENGTH: 8
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 15 gaaggcta                                                                           8

<210> SEQ ID NO 16
<211> LENGTH: 8
<212> TYPE: DNA
<213> ORGANISM: Artificial Sequence
<220> FEATURE:
<223> OTHER INFORMATION: Description of Artificial Sequence:example
      sequence illustrating a computational methodology

```
<400> SEQUENCE: 16 atccgaaa                                                              8

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 17
ccgcttacgc                                                           10

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 18 ctttaccgt                                                             9

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 19
cccgtttacc                                                           10

<210> SEQ ID NO 20
<211> LENGTH: 8
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 20 aatttgca                                                              8

<210> SEQ ID NO 21
<211> LENGTH: 9
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 21 cgctttccc                                                             9

<210> SEQ ID NO 22
<211> LENGTH: 9
<212> TYPE: DNA
<213> ORGANISM: Artificial Sequence
<220> FEATURE:
<223> OTHER INFORMATION: Description of Artificial Sequence:example
      sequence illustrating a computational methodology
```

```
<400> SEQUENCE: 22 ggtaaactt                                                                    9

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 23
agtcccccat                                                                  10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 24
catacaatgc                                                                  10

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 25
cccccccccc                                                                  10

<210> SEQ ID NO 26
<211> LENGTH: 9
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 26 cttggataa                                                                    9

<210> SEQ ID NO 27
<211> LENGTH: 9
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 27 gtggggtaa                                                                    9

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 28
```
acacaatgcg                                                          10

<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 29
cagttctagg                                                          10

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 30
aaggaggcag                                                          10

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 31
acacgatgcg                                                          10

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 32
tccatgtatt                                                          10

<210> SEQ ID NO 33
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 33
gtgtatgagc                                                          10

<210> SEQ ID NO 34
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 34

```
cgcggatatg                                                            10

<210> SEQ ID NO 35
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 35
aactatgatc                                                            10

<210> SEQ ID NO 36
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 36
tcattgtgag                                                            10

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 37
ggatttagct                                                            10

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence:example
      sequence illustrating a computational methodology

<400> SEQUENCE: 38
cgtgggaact                                                            10
```

METHOD AND SYSTEM FOR COMPUTATIONALLY IDENTIFYING CLUSTERS WITHIN A SET OF SEQUENCES

TECHNICAL FIELD

The present invention relates to computational methodologies for identifying common sub-patterns within a set of patterns and, in particular, to identifying DNA sequences that correspond to protein binding sites by computationally analyzing large sets of relatively short oligonucleotide sequences that represent potential protein binding sites.

BACKGROUND OF THE INVENTION

The molecular blueprint for a living eukaryotic organism is stored in double-stranded deoxyribose-nucleic acid ("DNA") molecules within the nucleus of each cell of the organism. Each double-stranded DNA molecule comprises a large number of templates, called genes, that each specifies the composition of a protein molecule and a large number of regulatory regions and additional regions for which a functionality has not yet been identified. Protein molecules are synthesized from the gene templates in a two-step process. In the first step, called transcription, the gene is copied to produce a molecule of messenger ribose-nucleic acid ("RNA"). In the second step, called translation, a protein molecule is synthesized according to the information contained in the messenger RNA molecule. The regulatory regions of a double-stranded DNA molecule act as switches, brakes, and accelerators for controlling the transcription of genes into messenger RNA molecules, thereby controlling the rate of synthesis of the various proteins specified by the genes. Proteins serve as catalysts for the myriad of chemical actions that occur within living organisms, as well as structural and mechanical elements from which living organisms are formed. Thus, the regulation of protein formation via the regulatory regions of double-stranded DNA molecules controls the development, structure, and dynamic composition of living cells.

Both proteins and DNA molecules are long linear polymers synthesized from a relatively small number of component molecules, or subunits. FIG. 1 shows the twenty amino acid subunits from which protein molecules are commonly synthesized. Each amino acid subunit has an α-carboxyl group (e.g., the α-carboxyl group 101 of the amino acid lysine 103), an α-amino group (e.g., the α amino group 105 of the amino acid lysine 103), and a side chain (e.g., the γ-amino propyl side chain 107 of the amino acid lysine 103), all attached to an α-carbon atom (e.g., the α-carbon 109 of the amino acid lysine 103). FIG. 2 shows a small polypeptide polymer built from four amino acids. The polypeptide polymer 200 has a free α-amino group 202 at the N-terminal end 204 of the polypeptide polymer 200 and a free α-carboxyl group 206 at the C-terminal end 208 of the polypeptide polymer 200. The polypeptide polymer 200 is composed from the following amino acids: (1) alanine 210; (2) tyrosine 212; (3) aspartic acid 214; and (4) glycine 216. A protein comprises one or more polypeptide polymers, similar to the polypeptide polymer 200 shown in FIG. 2, each generally comprising tens to hundreds of amino acid subunits.

The amino acid subunits within a protein are normally designated by either three-letter symbols or by one-letter symbols. Table 1, below, lists both the three-letter symbols and the one-letter symbols corresponding to each of the amino acids:

| Amino Acid | Three Letter Symbol | One Letter Symbol |
|---|---|---|
| Alanine | Ala | A |
| Argine | Arg | R |
| Asparagine | Asn | N |
| Aspartic acid | Asp | D |
| Asparagine or aspartic acid | Asx | B |
| Cysteine | Cys | C |
| Glutamic acid | Glu | E |
| Glutamine | Gln | Q |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A protein can be chemically described by writing its amino acid subunit sequence using either the three-letter symbols or the one-letter symbols, listed in Table 1, for the amino acids of the protein, starting from the N-terminal amino acid on the left side and ending with the C-terminal amino acid on the right side. For example, the polypeptide polymer displayed in FIG. 2 can be described either as "ALA-TYR-ASP-GLY" or "AYDG." Although a protein can be conceptualized as a linear sequence of amino acids, the protein molecule in solution normally folds into a complex and specific three-dimensional shape. FIG. 3 shows a representation of the three-dimensional shape of a relatively small, common protein.

DNA molecules, like proteins, are linear polymers. DNA molecules are synthesized from only four different types of subunit molecules: (1) deoxy-adenosine, abbreviated "A"; (2) deoxy-thymidine, abbreviated "T"; (3); deoxy-cytosine, abbreviated "C"; and (4) deoxy-guanosine, abbreviated "G." FIG. 4 illustrates a short DNA polymer 400, called an oligomer, composed of the following subunits: (1) deoxy-adenosine 402; (2) deoxy-thymidine 404; (3) deoxy-cytosine 406; and (4) deoxy-guanosine 408. When phosphorylated, these subunits of the DNA molecule are called nucleotides, and are linked together through phosphodiester bonds 410–415 to form the DNA polymer. The DNA molecule has a 5' end 418 and a 3' end 420. A DNA polymer can be chemically characterized by writing, in sequence from the 5' end to the 3' end, the single letter abbreviations for the nucleotide subunits that together compose the DNA polymer. For example, the oligomer 400 shown in FIG. 4 can be chemically represented as "ATCG." A nucleotide comprises a purine or pyrimidine base (e.g. adenine 422 of the deoxy-adenylate nucleotide 402), a deoxy-ribose sugar (e.g. ribose 424 of the deoxy-adenylate nucleotide 402), and a phosphate group (e.g. phosphate 426) that links the nucleotide to the next nucleotide in the DNA polymer.

The DNA polymers that contain the organizational information for living organisms occur in the nuclei of cells in pairs, called double-stranded DNA helixes. One polymer of the pair is laid out in a 5' to 3' direction, and the other polymer of the pair is laid out in a 3' to 5' direction. The two DNA polymers in the double-stranded DNA helix are therefore described as being anti-parallel. The two DNA polymers, or strands, within a double-stranded DNA helix are bound to each other through hydrogen bonds. Because of a number of chemical and topographic constraints, a deoxy-adenylate subunit of one strand must hydrogen bond to a deoxy-thymidylate subunit of the other strand, and a deoxy-guanylate subunit of one strand must hydrogen bond to a deoxy-cytidylate subunit of the other strand.

FIG. 5 illustrates the hydrogen bonding that joins two anti-parallel DNA strands. The first strand 502 occurs in the 5' to 3' direction and contains a deoxy-adenylate subunit 504 and a deoxy-guanylate subunit 506. The second, anti-parallel strand 508 contains a deoxy-thymidylate subunit 510 and a deoxy-cytidylate subunit 512. The deoxy-adenylate subunit 504 is joined to the deoxy-thymidylate subunit 510 through hydrogen bonds 514 and 516. The deoxy-guanylate subunit 506 is joined to the deoxy-cytidylate subunit 512 through hydrogen bonds 518–522.

The two DNA strands linked together by hydrogen bonds form the familiar helix structure of the double-stranded DNA helix. FIG. 6A illustrates a short section of a DNA double helix 600 comprising a first strand 602 and a second, anti-parallel strand 604. A deoxy-guanylate subunit in one strand 606 is always paired with a deoxy-cytidylate subunit 608 in the other strand, and a deoxy-thymidylate subunit in one strand 610 is always paired with a deoxy-adenylate subunit in the other strand 612. FIG. 6B shows a representation of the two strands illustrated in FIG. 6A using the single-letter designations for the nucleotide subunits. The first strand 614 (602 in FIG. 6A) is written in the familiar 5' to 3' direction, and the second strand 616 (604 in FIG. 6A) is written in the 3' to 5' direction in order to clearly show the subunit pairings between the two strands. These pairings are called base pairs because the hydrogen bonding occurs between the purine and pyrimidine bases of the nucleotide subunits. Nucleotide subunits are often referred to as bases. There is a "C" (e.g., 618) in the second strand directly opposite from each "G" (e.g., 620) in the first strand, an "A" (e.g., 622) in the second strand directly opposite from each "T" (e.g., 624) in the first strand, a "T" (e.g., 626) in the second strand directly opposite from each "A" (e.g., 628) in the first strand, and a "G" (e.g., 630) in the second strand directly opposite from each "C" (e.g., 632) in the first strand. Thus, knowing the sequence for the first strand, one can immediately determine and write down the sequence for the second strand. DNA base-pair sequences are always written in the 5' to 3' direction. The second strand 634 is shown properly written in the 5' to 3' direction as the last sequence in FIG. 6B. When written in this fashion, the second strand is said to be the reverse complement of the first strand. Thus, the "G" 636 on the left or 5' end of the second strand 634 is paired in the DNA double helix 600 with the "C" 638 at the right or 3' end of the first strand 614.

As described above, the synthesis of proteins from gene templates is controlled through regulatory regions of DNA molecules. A large number of different types of DNA-binding proteins bind to these regulatory regions of DNA molecules and, by so doing, initiate, promote, inhibit, or prevent the synthesis of one or more specific genes. FIG. 7A illustrates the binding of a dimeric, or two-polymer DNA-binding protein 702 to a specific regulatory region 704 of a double-stranded DNA helix 706. In general, a number of amino acid subunits of a DNA-binding protein hydrogen bond to nucleotide subunits of the DNA molecule to affect the binding of the DNA-binding protein to the DNA double helix. FIG. 7B illustrates two hydrogen bonds 708 and 710 between an amino acid subunit 712 of a DNA-binding protein 714 and a nucleotide subunit 716 of a DNA double helix 718 viewed down the central axis of the DNA double helix.

FIG. 8 illustrates the spatial relationship between a gene and various regulatory regions of a DNA double helix that control transcription of the gene. The gene 802 is generally preceded by a promoter region 804 where various molecular components 806 are assembled in order to catalyze the synthesis of messenger RNA from the gene template. In addition, various regulatory DNA-binding proteins or assemblies of regulatory DNA-binding proteins 808–810 specifically bind to a number of regulatory regions of the DNA double helix 811–813 that are located at various distances along the DNA double helix from the gene 802. In general, the regulatory proteins may either increase the rate of gene transcription or decrease the rate of gene transcription, thus controlling the concentration of the protein specified by the gene within the cell. Each type of regulatory DNA-binding protein recognizes and binds to a specific sequence, or pattern, of base pairs within the regulatory region. These sequences, called binding sites, are generally less than twenty nucleotides in length.

The molecular state of a cell and of an entire living organism largely depends on the regulation of gene transcription by thousands of different regulatory DNA-binding proteins. Only one or several molecules of each different type of regulatory protein may occur in a cell at any given time. A cell thus contains a very complex mixture of regulatory DNA-binding proteins, and each regulatory DNA-binding protein may occur in the mixture at extremely small concentrations. Aberrations in the structures of certain regulatory DNA-binding proteins, or in the concentrations of certain regulatory DNA-binding proteins within cell nuclei, may underlie many different diseases and disorders, including developmental problems, inherited genetic disorders, and cancers. It is therefore a goal of biological sciences and of the biotechnology industry to identify and characterize the many different types of regulatory DNA-binding proteins.

There are a number of different approaches to identifying regulatory DNA-binding proteins. One such approach is called the multiplex selection technique, or "MuST™." The MuST technique is described in the following patent applications, which are hereby incorporated by reference in their entirety: U.S. patent application Ser. No. 08/590,571, filed Jan. 24, 1996, PCT application Serial No. PCT/US97101230, filed Jan. 24, 1997, and U.S. application Ser. No. 08/906,691 filed Aug. 6, 1997. In this method, a very large number of relatively short oligonucleotide DNA duplexes having random sequences are prepared and mixed together with a sample that contains various DNA-binding proteins. The random-sequence oligonucleotide duplexes generally have lengths of between eight and twelve base pairs. After the random-sequence oligonucleotide duplexes are mixed with the DNA-binding proteins, the DNA-binding proteins bind to specific oligonucleotide duplexes that contain base-pair sequences that the DNA-binding proteins recognize; or, in other words, a particular type of DNA-binding protein binds to those oligonucleotide duplexes that contain base-pair sequences identical or similar to the base pair sequence of the binding site within the regulatory region of the DNA double helix controlled by that DNA-binding protein. Various biochemical separation techniques are employed to separate the DNA-binding proteins bound to the oligonucleotide duplexes from unbound proteins, unbound oligonucleotide duplexes, and other molecules within the mixture. The bound DNA-binding protein/ oligonucleotide duplex pairs are then separated, the separated oligonucleotide duplexes are amplified by the polymerase chain reaction ("PCR") technique and, finally, the two strands of the oligonucleotide duplexes are separated and identified by sequence analysis. The result of the analysis is a list of nucleotide sequences of single strands of the oligonucleotide duplexes that were bound by DNA-binding proteins in the mixture.

DNA-binding proteins have varying specificities for base-pair sequences. Each different type of DNA-binding protein generally recognizes and binds to a particular binding site within a particular regulatory region of a DNA double helix. The binding site comprises a specific sequence of base pairs within the DNA double helix. However, a particular DNA-binding protein may recognize and bind to any number of sequences similar to the sequence of the binding site which the DNA-binding protein normally recognizes and to which the DNA-binding protein binds. Base-pair sequence analysis is conducted on single strands of DNA rather than on DNA duplexes. A DNA-binding site for a particular DNA-binding protein will be therefore characterized, following an analysis of oligonucleotide sequences produced by the MuST technique, by a set of similar sequences corresponding to one strand of the duplex regions bound by the DNA-binding protein and by a set of similar sequences corresponding to the other strand of the duplex regions bound by the DNA-binding protein. Because the two sets of sequences are related by reverse complementation, the original two sets are merged into a single set of sequences by applying reverse complementation to the sequences in one of the original two sets. Because the oligonucleotide duplexes employed in the MuST technique are randomly generated, the first base pair of the sequence recognized by a DNA-binding protein may not correspond to the first base pair of the oligonucleotide duplex, but may occur at many different positions within the oligonucleotide duplex. Generally, a DNA-binding protein may bind to some minimum number of base pairs that compose a sub-sequence of the sequence of the binding-site. Because the MuST oligonucleotide sequences are random, a particular binding site for a particular DNA-binding protein will be characterized within the set of sequences produced by the MuST technique by a set of oligonucleotide sequences that contain sub-sequences identical or similar to sub-sequences of the binding site sequence greater than or equal in length to some minimum number of nucleotides.

FIG. 9 illustrates the characterization of various clusters representing potential DNA-binding sites from a set of sequences produced by the MuST technique. A set of 21 sequences 902 represents the oligonucleotide sequences identified by the MuST technique. As commonly applied to cell extracts containing DNA-binding proteins, the MuST technique may produce a set of many thousands of sequences. FIG. 9 is intended to illustrate the general concept of MuST sequence analysis rather than provide an actual example.

Examination of the set of MuST sequences 902 does not immediately reveal a pattern of related sequences. However, as a result of an exhaustive comparison of each sequence in the set of sequences 902 to the other sequences in the set of sequences 902 by shifting the sequences relative to one another, and identifying common sub-sequences, five clusters of related sequences 904–908 can be identified. Each sequence of the first cluster of sequences 904 contains a common seven-base-pair sub-sequence "GTTTACC" or some very similar variation of that sub-sequence. These common sub-sequences within each of the sequences of the first cluster 904 are indicated by box 906. Note that the common sub-sequence occurs towards the end of sequence 13 (908 in FIG. 9) in which the final two nucleotides of the common sub-sequence are missing. It should also be noted that, in some sequences, one or more nucleotides of the common sub-sequence have been substituted with another. For example, sequence 18 (910 in FIG. 9) contains an initial "C" 912 rather than a "G." Sequence 18 (910 in FIG. 9) is shifted three positions to the right relative to sequence 17 (914 in FIG. 9) and is shifted four places to the right relative to sequence 19 (916 in FIG. 9) in order that the common sub-sequence of sequence 18 aligns with the common sub-sequences of sequences 17 and 19. Sequence 22 (918 in FIG. 9) in the original set of sequences 902 does not initially appear to have a portion in common with any of the other sequences. However, the reverse complement of sequence 22 (918 in FIG. 9) is identical with sequence 1 (920 in FIG. 9) and is therefore included, along with sequence 1, in the first cluster 904. The lines between the sequences in the set of MuST sequences 902 and the sequences within clusters 904–908 (e.g., line 924) show a mapping from the original MuST sequences to the five clusters. It is this mapping between oligonucleotide sequences and clusters, including the alignments and reverse complementation required to match the common sub-sequences within the sequences of a cluster, that is the goal of the computational technique of the described embodiment of the present invention.

Each of the clusters 904–908 that are identified from the original set of MuST sequences 902 represents a potential DNA-protein binding site. The number of sequences within a cluster may be related to the concentration in the original cell extract mixture of the DNA-binding protein that recognizes the common sequence within that cluster. Clusters with one or a few sequences, such as cluster 2 (905 in FIG. 9) and cluster 4 (907, in FIG. 9) may represent a binding site to which an extremely rare or low-concentration regulatory DNA-binding protein binds, or may possibly represent an artifact arising from experimental methodologies.

Once a binding site has been identified by analysis of the MuST sequences, that binding site can be compared to data bases of known binding sites to determine whether the binding site has been previously characterized. The DNA-binding proteins that bind to a particular binding site can be purified from complex mixtures by various biochemical techniques. The sequence of amino acids that together compose the one or more polymers of the DNA-binding protein can be determined from the purified protein by biochemical protein sequence analysis techniques. Once the sequence for a DNA-binding protein has been determined, that sequence can be compared to data bases of known protein sequences or can serve as the basis for the identification of the gene or genes within an organism's DNA molecules that serve as a template for the synthesis of that DNA-binding protein. These various characterizations of the DNA-binding protein may eventually lead to the identification of diseases associated with aberrations in the structure of the protein or in the control of the expression of the gene that is the template for the DNA binding protein. These various characterizations may also lead to various ameliorative therapies that can be employed to treat such diseases.

SUMMARY OF THE INVENTION

An embodiment of the present invention provides a method and system for computationally analyzing an initial set of oligonucleotide sequences in order to identify groups or subsets of sequences that contain common sub-sequences. The initial set of oligonucleotide sequences may be produced by various biochemical techniques and may correspond to a number of different DNA-binding sites within one or more double-stranded DNA duplexes. The common subsequences may be offset from each other within the initial sequences, requiring the sequences of the initial set of oligonucleotide sequences to be aligned in order to identify the common sub-sequences. Reverse complementation may also be applied to a sequence in order to reveal the common sub-sequence that is contained within the sequence.

In one embodiment of the present invention, the common sub-sequence within a subset of sequences, or cluster, that is identified as a potential binding site is modeled by a numerical construct called an information weight matrix. Each sequence in the initial set of sequences is separately analyzed with respect to all other sequences within the initial set of sequences. A sequence to be analyzed is placed within a new cluster and an initial information weight matrix is calculated for that cluster. Then, other sequences from the initial set of sequences are added to the cluster and the information weight matrix of the cluster is re-computed for the cluster until the information content of the information weight matrix falls below a threshold value. The next sequence chosen for addition to the cluster is a sequence that is not already included in the cluster and that has the highest information content with respect to the information weight matrix calculated for the cluster.

BRIEF DESCRIPTION OF THE DRAWINGS

FIGS. 11A & 11B shows a frequency matrix and an information weight matrix.

FIG. 12 shows an initial list of sequences obtained from a biochemical technique, such as the MuST technique.

FIG. 13A shows a first cluster identified from the sequences of FIG. 12.

FIG. 13B shows a frequency matrix calculated from the first cluster of FIG. 13A.

FIG. 13C shows an information weight matrix calculated from the values in the frequency matrix of FIG. 13B.

FIG. 14A shows a cluster having two sequences.

FIG. 14B shows a frequency matrix calculated from the cluster of FIG. 14A.

FIG. 14C shows an information weight matrix calculated from the values of the frequency matrix shown in FIG. 14B.

FIG. 15A shows a cluster having three sequences.

FIG. 15B shows a frequency matrix calculated from the cluster of FIG. 15A.

FIG. 15C shows an information weight matrix calculated from the values in the frequency matrix of FIG. 15B.

DETAILED DESCRIPTION OF THE INVENTION

Embodiments of the present invention provide a method and system for analyzing a set of linear sequences in order to identify subsets of the set of linear sequences that share common sub-sequences. One embodiment of the present invention is directed, for example, to identifying potential DNA-binding sites by analyzing a set of oligonucleotide sequences and organizing the set of oligonucleotide sequences into subsets of oligonucleotide sequences, called clusters, that contain similar sequences. Each cluster may correspond to a DNA-binding site. The method of this embodiment separately analyzes each sequence selected from the initial set of sequences. The selected sequence is considered to be the first member of a new cluster. The cluster is modeled by an abstract numerical construct called an information weight matrix. The method successively chooses additional sequences from the initial set of sequences to add to the cluster. At any point in the analysis of a given cluster, the next sequence chosen to be added to the cluster is the sequence that has the highest information content with respect to the current information weight matrix that describes the cluster. Sequences are successively added to the cluster until the information content of the information weight matrix that describes the cluster falls below a particular threshold value. At that point, the cluster is complete. The analysis then continues with a different sequence selected from the set of initial sequences. The result of the analysis of this embodiment of the present invention is a set of clusters.

While the embodiment described below is directed toward identifying potential DNA-binding sites from a set of oligonucleotide sequences, the method and system of the present invention may be employed, in other embodiments, to analyze different types of sequences. For example, the sequences of amino acid subunits within protein polymers might be analyzed by an embodiment of the present invention in order to identify common or conserved amino acid subunit sub-sequences within the polymers that correspond to common structural features within a family of proteins. As another example, the words of a language, represented as sequences of letters, might be analyzed by a different embodiment of the present invention in order to identify common root words from which families of words have been derived.

Figure 1:
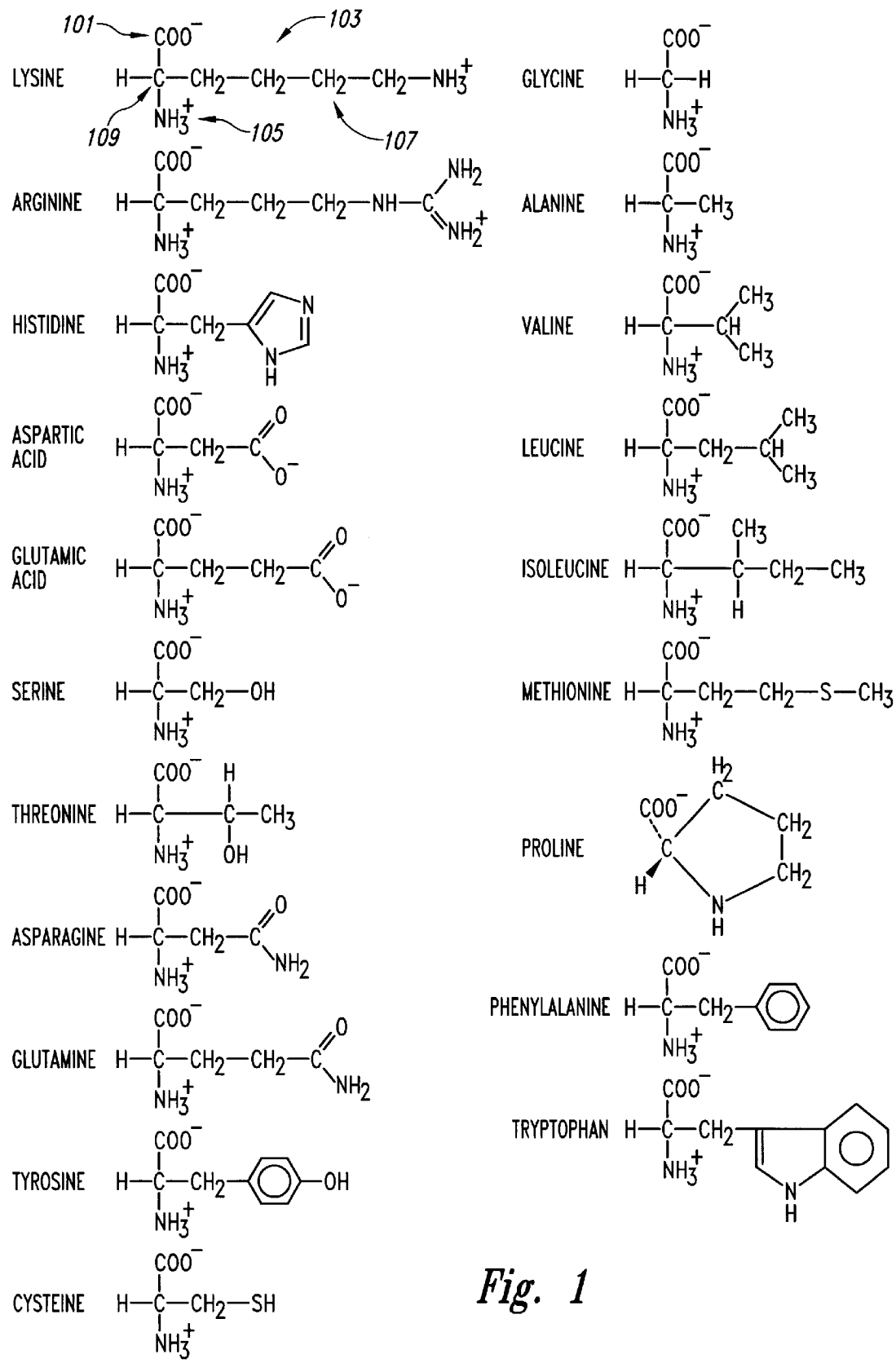
FIG. 1 shows twenty amino acid subunits from which protein molecules are commonly synthesized.
Figure 2:
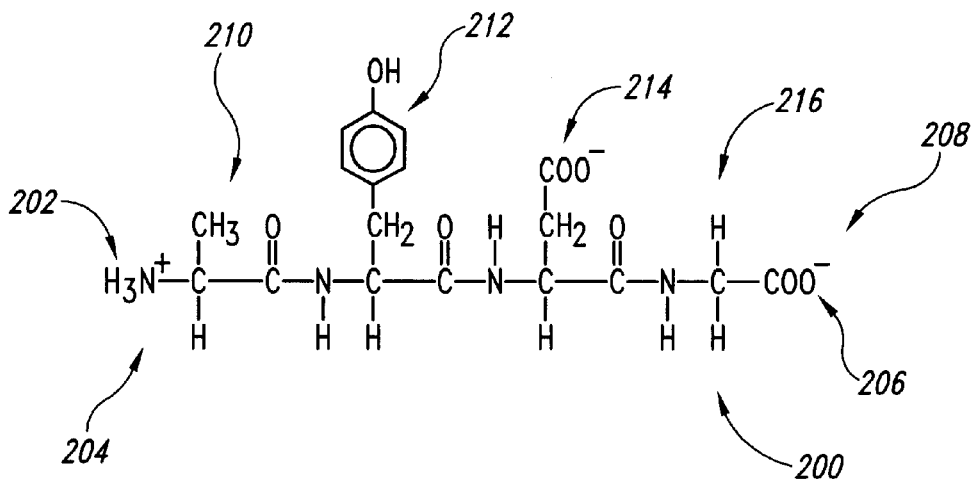
FIG. 2 shows a small polypeptide polymer built from four amino acids.
Figure 3:
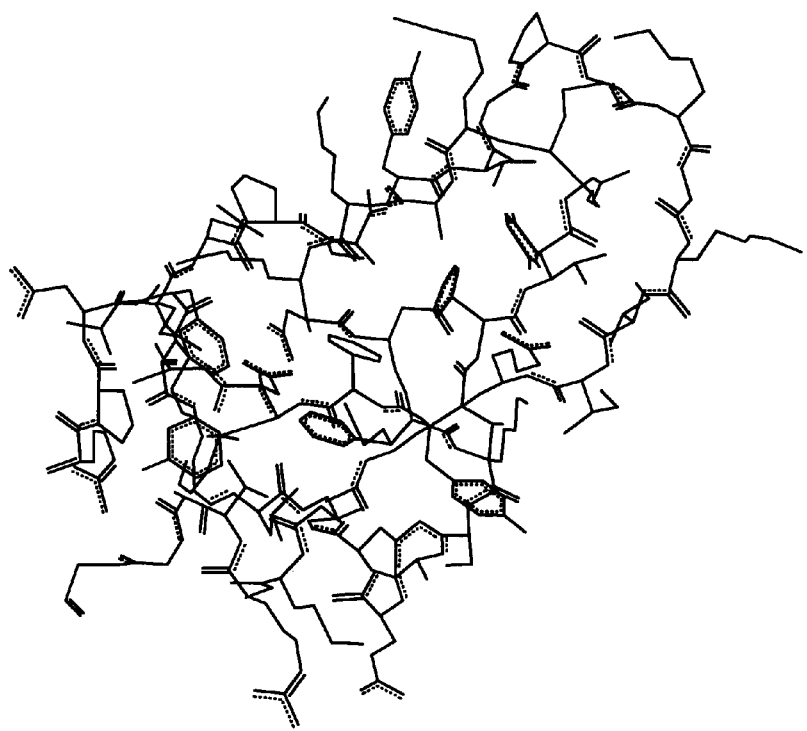
FIG. 3 shows a representation of the three-dimensional shape of one type of protein.
Figure 4:
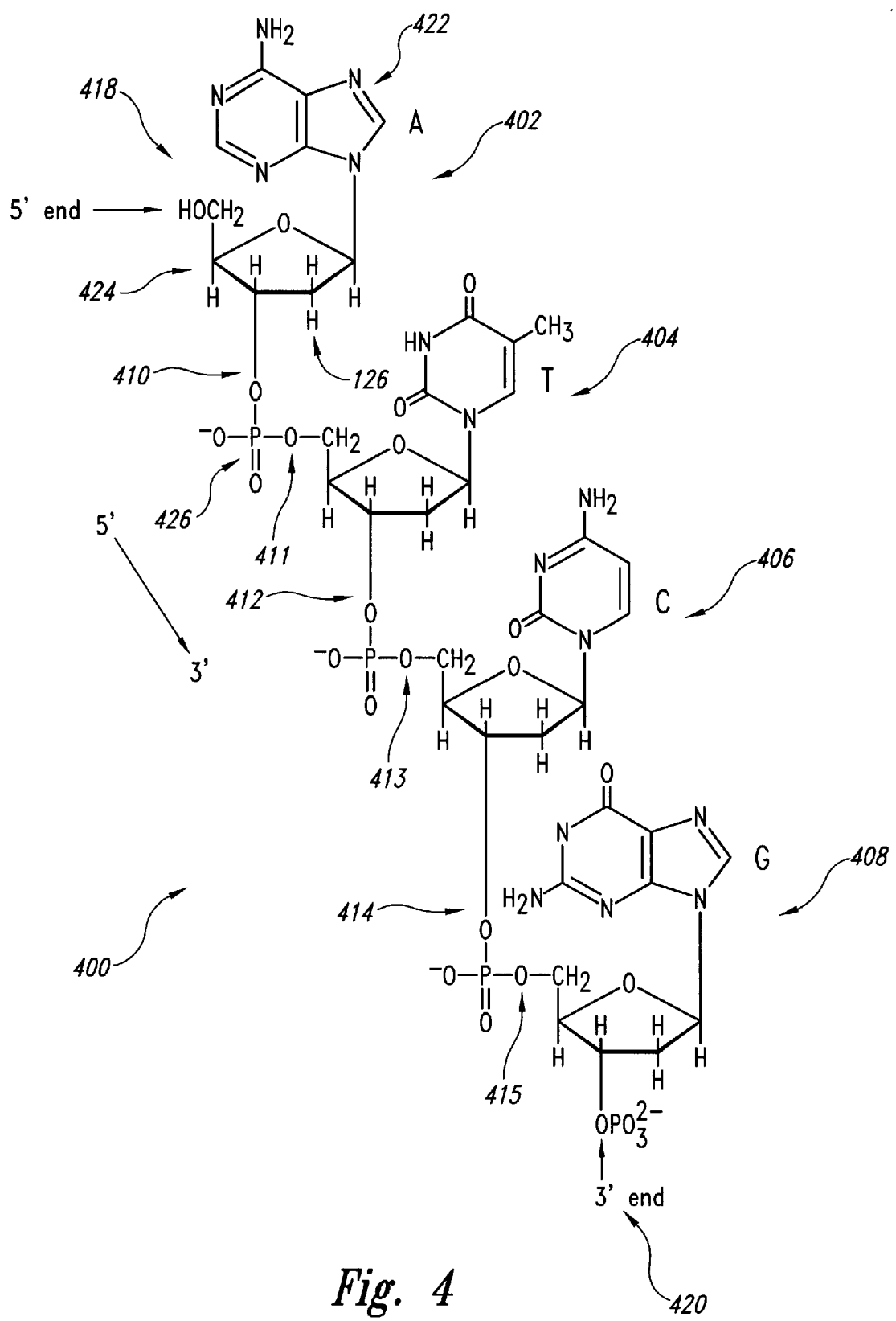
FIG. 4 illustrates a short DNA oligomer.
Figure 5:
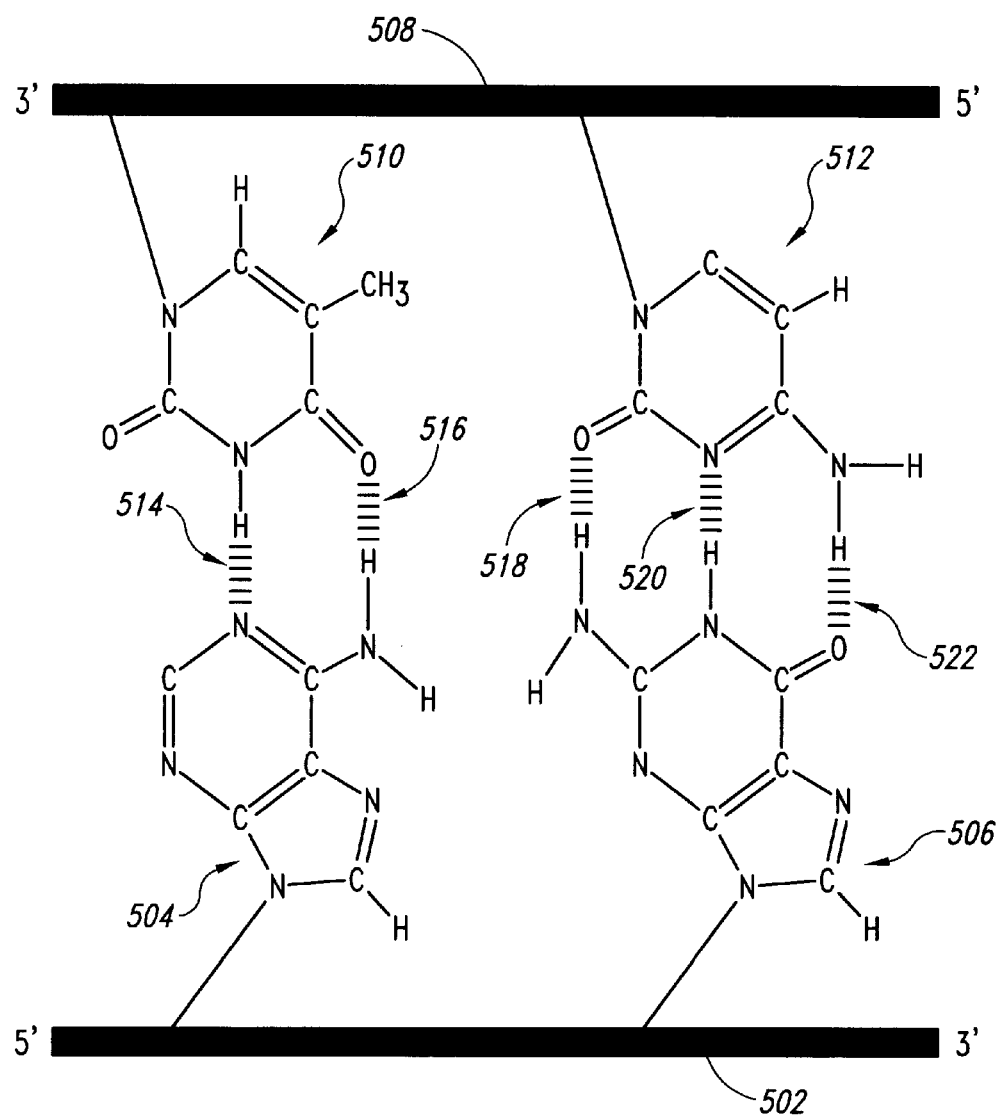
FIG. 5 illustrates the hydrogen bonding that joins two anti-parallel DNA strands.
Figure 6A:
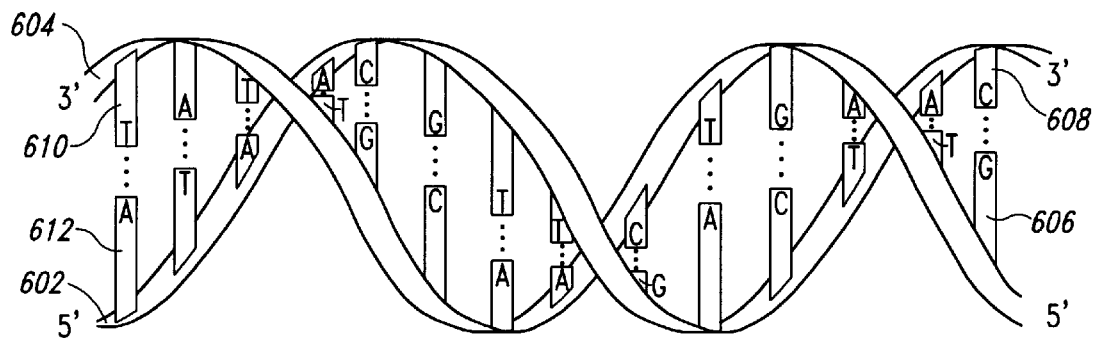
FIG. 6A illustrates a short section of a DNA double helix.
Figure 6B:
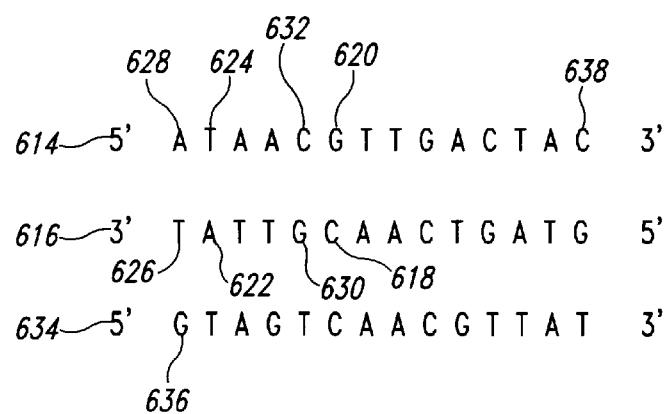
FIG. 6B shows a representation of the two DNA strands illustrated in FIG. 6A using single-letter designations for the nucleotide subunits.
Figure 7A:
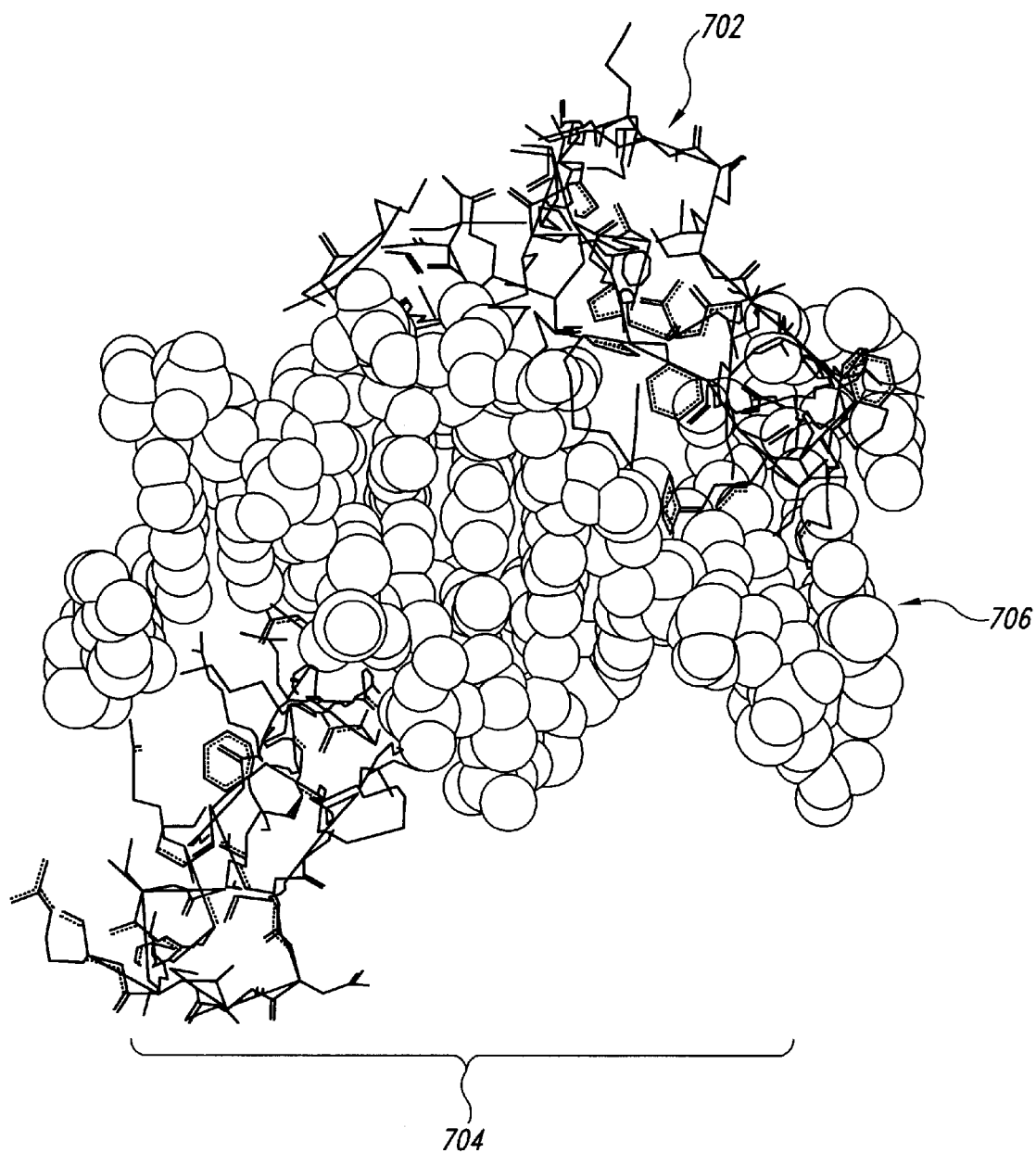
FIG. 7A illustrates the binding of a DNA-binding protein to a specific regulatory region of a double-stranded DNA helix.
Figure 7B:
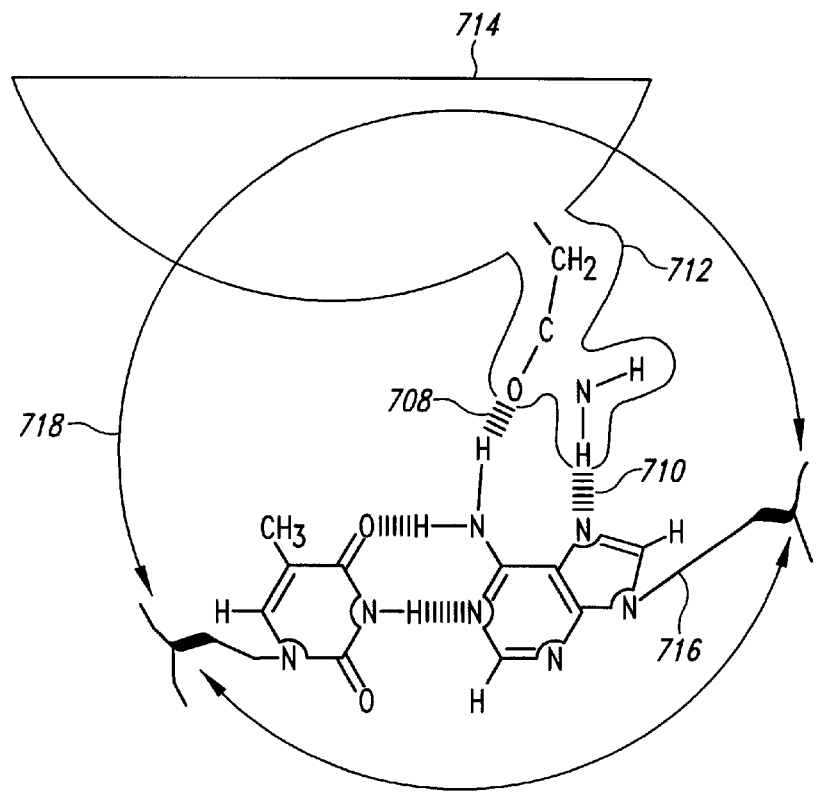
FIG. 7B illustrates two hydrogen bonds between an amino acid subunit of a DNA-binding protein and a nucleotide subunit of a DNA double helix.
Figure 8:
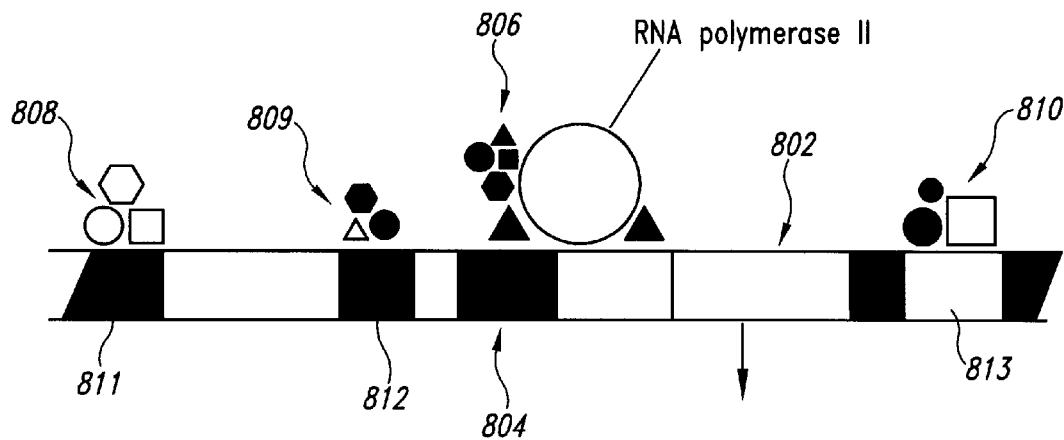
FIG. 8 illustrates the spatial relationship between a gene and various regulatory regions of a DNA double helix that control transcription of the gene.
Figure 9:
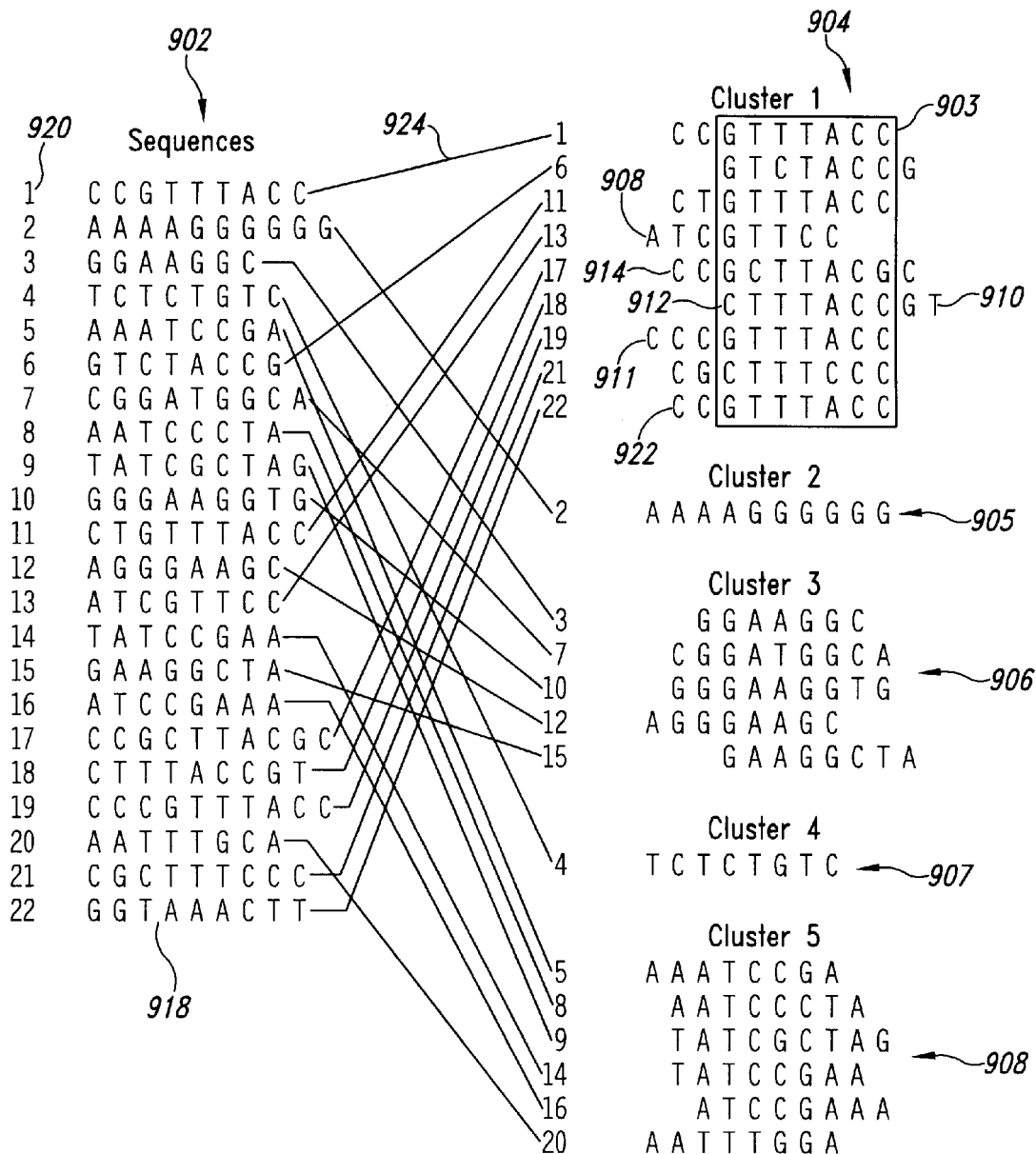
FIG. 9 illustrates the characterization of clusters representing potential various DNA-binding sites from a set of sequences produced by the MuST technique.
Figure 10A:
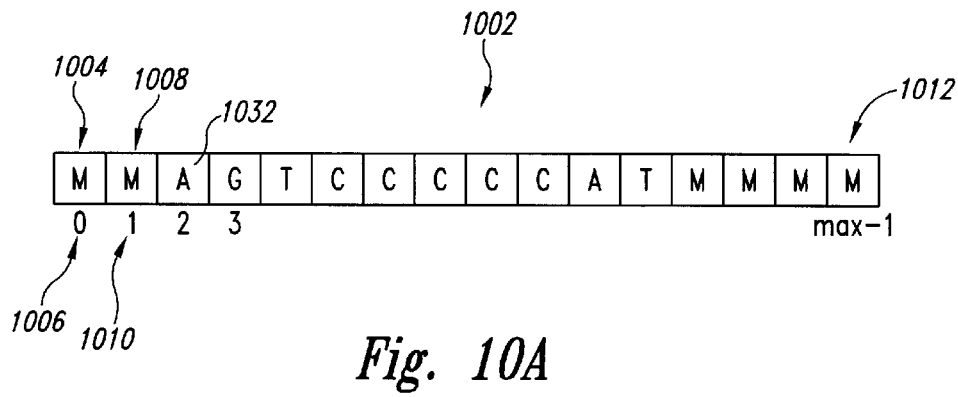
FIG. 10A shows the representation of the oligonucleotide sequence "AGTCCCCCAT" within a character array.

Each oligonucleotide sequence from the initial set of sequences produced by the MuST technique, or by a similar technique, is represented naturally within a computer as an array of characters. The four nucleotide subunits are represented by the letters "A," "G," "T," and "C." Because the sequences are shifted left and right for alignment purposes during the analysis, a particular sequence is normally stored within a character array larger than the sequence, and the letter "M" is placed within the empty or blank positions within the character array to the left and to the right of the actual oligonucleotide sequence. FIG. 10A shows the representation of the oligonucleotide sequence "AGTCCCCCAT" within a character array. The character array 1002 has positions for a particular number of characters. In the case of the character array 1002 shown in FIG. 10A, there are 16 positions. Each position has an index. The first position 1004 has index "0" 1006. The second position 1008 has index "1" 1010. The remaining positions are successively numbered up to the final position 1012 that has index "15," or one less than the maximum number of positions in the character array, "max−1."

Figure 10B:
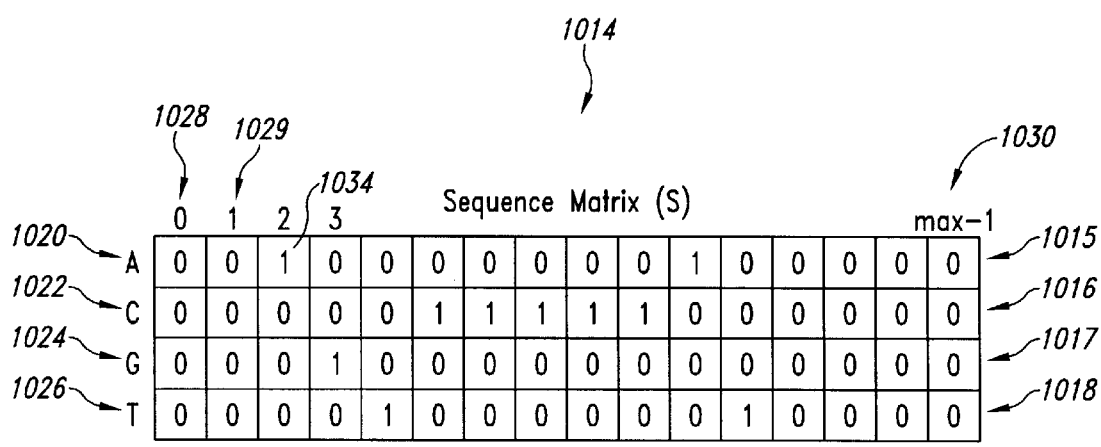
FIG. 10B shows a sequence matrix representing the oligonucleotide sequence "AGTCCCCCAT" of FIG. 10A.

The sequence stored in the character array of FIG. 10A can be alternatively represented by a matrix. FIG. 10B shows a sequence matrix representing the oligonucleotide sequence "AGTCCCCCAT" of FIG. 10A. The sequence matrix 1014 has four rows 1015–1018 and 16 columns. The rows are indexed by single character designations for oligonucleotide subunits: "A" 120, "C" 122, "G" 124, and "T" 126. The columns are indexed by monotonically increasing integers "0" through "15", for example, column "0" 128, column "1" 129, and the final column 15 130. Comparing the character array of FIG. 10A with the sequence matrix of FIG. 10B, it is seen that, for each position within the character array containing a single character designation of an oligonucleotide subunit, there is a value "1" stored in the cell of the sequence matrix in the row indexed by the oligonucleotide designation and in the column indexed by the position of the oligonucleotide designator within the character string. For example, nucleotide "A" in position "2" of the character array 1032 corresponds to the value "1" in the cell of the sequence matrix 1034 in row "A" and in column "2."

In the following discussion, cells within a matrix are indexed with two values: a first value corresponding to the row containing the cell and a second value corresponding to the column containing the cell. The two indices are enclosed within parentheses as a subscript that follows a subscripted, capital-letter designation for the matrix. For example, the sequence matrix of FIG. 10B is designated "$S_k$" and cell 1034 of the sequence matrix is designated as "$S_{k(A,2)}$." In this convention, "S" refers to a set of sequences, "$S_k$" refers to the k-th sequence within the set of sequences "S," and "$S_{k(A,2)}$" refers to the cell of the k-th sequence within the set of sequences, "$S_k$," in row "A" and in column "2." The character string representation of an oligonucleotide sequence is normally employed within a computer program, but the sequence matrix representation is convenient for expressing various mathematical operations that will be described below.

A cluster constructed via the analysis of the initial set of oligonucleotide sequences is mathematically described as an information weight matrix. The concept of an information weight matrix is described in U.S. patent application Ser. No. 08/494,115, filed Jun. 23, 1995, and PCT application Serial No. 96/11088, filed Jun. 21, 1996, both hereby incorporated by reference in their entireties. The information weight matrix is essentially a mathematical model of a cluster. The information weight matrix is calculated from a frequency matrix which describes the frequency that each particular type of nucleotide subunit occurs at each position within the sequences included in a cluster. FIG. 11 shows a frequency matrix, designated by the letter "F," and an information weight matrix, designated by the letter "I." The frequency matrix "F" 1102 has five rows and sixteen columns. The first four rows are indexed by the single letter designations for nucleotide subunits and the fifth row is designated by the letter "M," which represents a blank or empty position within the character array in which a sequence is stored. There is one column in the frequency matrix for every possible position within a sequence. In FIGS. 10 and 11, sixteen has been chosen as the maximum number of characters within the character array representation of a sequence. It should be noted that this number is chosen to be somewhat greater than the maximum oligonucleotide sequence to be considered in the analysis to allow for left and right shifting of a sequence for alignment purposes. If oligonucleotide sequences having twelve nucleotide subunits are being analyzed, and left and right alignment shifts of up to four positions are desired, then each sequence could be represented by a character array having twenty positions. In this case, the frequency matrix and the information weight matrix would each have twenty columns. The information weight matrix 1104 has four rows corresponding to each of the four possible nucleotide subunits and sixteen columns corresponding to the sixteen positions within a character array storing the sequence.

The frequency matrix "F" 1102 stores the frequencies of the occurrence of a given nucleotide subunit at a given position within all of the sequences that currently compose a cluster. The contents of a given cell $F_{(i,j)}$ that occurs at the intersection of row i and column j of the frequency matrix F, where i="A", "C", "G", or "T" is mathematically expressed as follows:

$$F_{(i,j)} = \frac{\sum_{k=0}^{N-1} S_{k(i,j)}}{N}$$

where N is the number of sequences included in the cluster and $S_k$ is the k-th sequence of the cluster. For the final row of the frequency matrix F, where i="M," the values within a cell in column "j" is given by the following formula:

$$F_{(M,j)} = 1 - \sum_{i=A}^{T} F_{(i,j)} = 1 - \frac{\sum_{i=A}^{T}\sum_{k=0}^{N-1} S_{k(i,j)}}{N}$$

Note that the frequencies that occur as the values in the cells of the frequency matrix range in value from 0 to 1 and that all of the frequencies in a particular column will sum to the value "1.0." If, for example, there were four sequences currently in a cluster, and each sequence had a different nucleotide subunit in the first position of the sequence, then the values in the first column of the frequency matrix would be as follows: $F_{(A,0)}=0.25$ $F_{(C,0)}=0.25$, $F_{(G,0)}= 0.25$, $F_{(T,0)}=$ 0.25, and $F_{(M,0)}=0.0$. In other words, the frequency of occurrence of each of the four nucleotide subunits in the four-sequence cluster would be 0.25, or twenty-five percent, and, since all of these sequences have a nucleotide subunit in the first position, the frequency of no nucleotide occurring in the first position of the sequences, $F_{(M,0)}$, would be zero.

The values in the cells of the information weight matrix I are generally calculated from values in corresponding cells of the frequency matrix F. To be exact, the value in a given cell of the information weight matrix $I_{(i,j)}$ depends on the value of the corresponding cell $F_{(i,j)}$ of the frequency matrix and possibly on the value of the cell $F_{(M,j)}$ of the M-th row and j-th column of the frequency matrix F by the following set of rules:

if $F_{(M,j)}=1$, then $I_{(i,j)}=0$ if $F_{(M,j)}=0$, then $I_{(i,j)}=2+\log_2 F_{(i,j)}$ if $F_{(M,j)}>0$ and $F_{(M,j)}<1$, then $I_{(i,j)}=2+\log_2 (F_{(i,j)}+F_{(M,j)}/4)$ Finally, any value calculated by the above set of rules that is less than −14.0 is set to −14.0. In other words, −14.0 is the floor value for the information weight matrix.

Both the frequency matrix and the information weight matrix are cumulative tallies or mathematical models of a cluster that are updated upon the addition of each new sequence to the cluster. A sequence is evaluated for inclusion in a cluster by determining the information content of the sequence with respect to the current information weight matrix. The information content of a sequence is given by the formula below:

$$\text{information content of sequence } k+1 = \sum_{j=0}^{\max-l} \sum_{i=A}^{T} S_{k+1_{(i,j)}} \cdot I_{(i,j)}$$

where sequence k+1, if added to the cluster, will become the (k+1)-th sequence of the cluster currently containing sequences 1 through k and modeled by information weight matrix "I." Note that the above formula is equivalent to superimposing the sequence matrix describing the sequence to be added on top of the information weight matrix and selecting and adding together all the values in the information weight matrix in cells overlaid by cells of the sequence matrix that contain the value "1." Sequences are successively added to the cluster until the information content of the information weight matrix falls below some threshold value. The information content of the information weight matrix I is given by the following formula:

$$\text{information content of } I = \frac{\sum_{k=0}^{N-1} \text{information content of } S_k}{N}$$

In other words, the information content of the information weight matrix is the average of the information contents of all the sequences within the cluster with respect to the information weight matrix that models the cluster.

FIGS. 12, 13A–C, 14A–C & 15A–C illustrate the frequency matrices and the information weight matrices calculated for a building cluster. FIG. 12 shows an initial list of sequences obtained from a biochemical technique, such as the MuST technique. The initial set of sequences 1201 comprises 15 different sequences. The first sequence of the set 1202 is selected as the first member of a first cluster. FIG. 13A shows this first cluster. The first cluster 1301 has an initial size of "1." The first sequence 1303 is shifted three positions to the right within the character array in which the first sequence is stored. The first sequence 1303 is therefore shown in FIG. 13A with three blank positions, designated with the letter "M," to the left of the first nucleotide of the sequence. FIG. 13B shows the frequency matrix calculated from the first cluster containing the first sequence. Because there is only one sequence in the cluster, the values in the frequency matrix must either be 1.0, indicating the presence of a nucleotide at a particular position, or 0.0, indicating that a particular nucleotide does not occur at that position. For example, the initial cytidylate nucleotide of the first sequence 1303 is represented in the frequency matrix by the value 1.0 in the cell 1304 in row "C" and in column "3." FIG. 13C shows the information weight matrix calculated from the values in the frequency matrix of FIG. 13B by the above-described set of rules.

FIGS. 14A–C show the cluster, frequency matrix, and information matrix following the addition of a second sequence, sequence "5" from the initial set of sequences, to the cluster. FIG. 14A shows the cluster following the addition of sequence "5." Note that sequence "5" 1404 is shifted to the right by one position with respect to sequence "1" 1402 in order to maximize the information content of sequence "5" and the information weight matrix. FIG. 14B shows the frequency matrix calculated from the cluster of FIG. 14A. FIG. 14C shows the information weight matrix calculated from the values of the frequency matrix shown in FIG. 14B. FIG. 15A shows the cluster following the addition of a third sequence. FIG. 15B shows the frequency matrix calculated from the cluster of FIG. 15A. FIG. 15C shows the information weight matrix calculated from the values in the frequency matrix of FIG. 15B.

Figure 16:
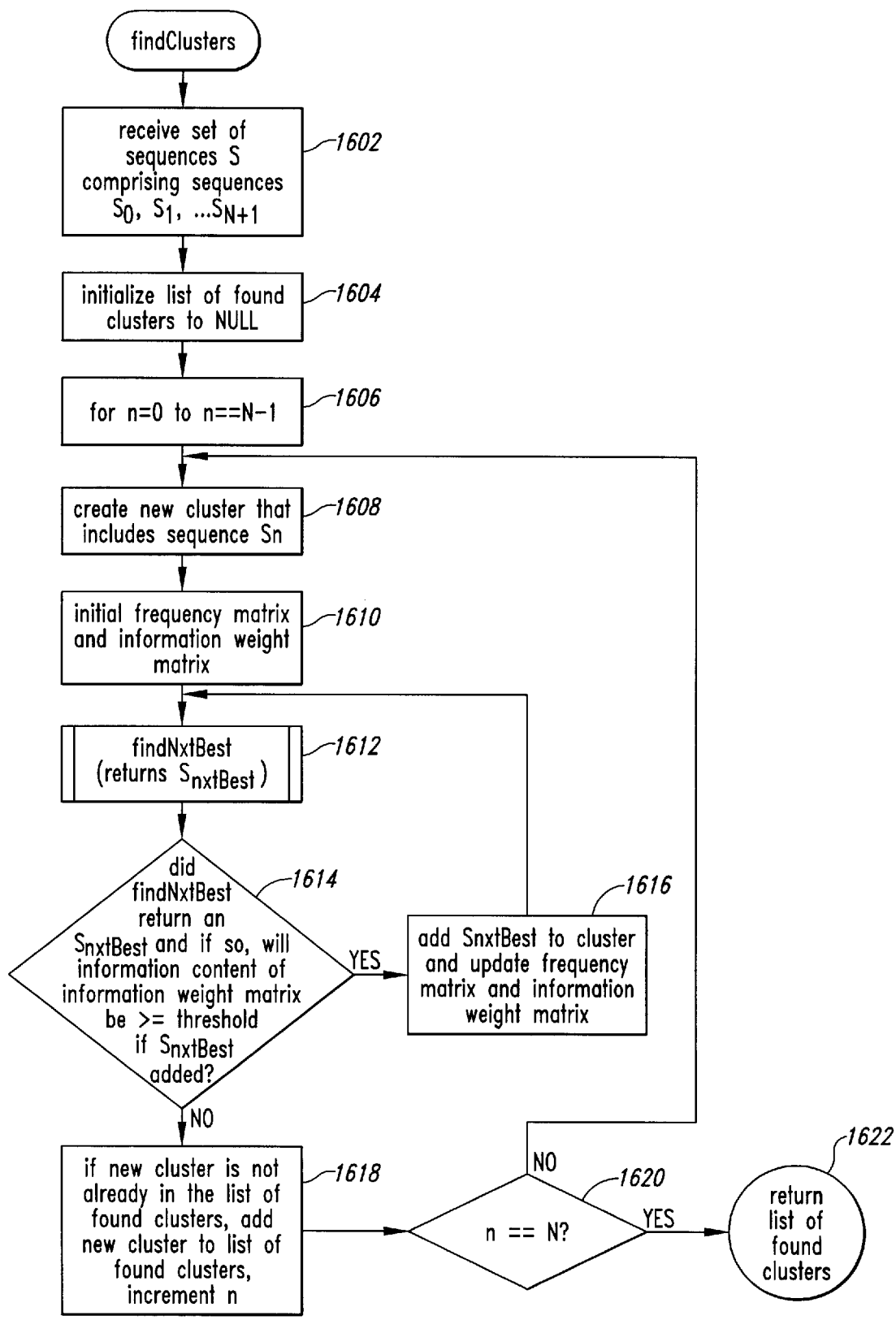
FIG. 16 is a flow-control diagram for the routine "findClusters" that implements one embodiment of the present invention.

FIG. 16 is a flow-control diagram for the routine "findClusters" that implements one embodiment of the present invention. In step 1602, the routine findClusters receives, as input, an initial set of sequences, "S," containing N sequences, $S_0$ through $S_{N-1}$. These sequences may be stored in character arrays, as shown in FIG. 11A, or may be represented in a variety of different alternative ways within a computer memory. In step 1604, the routine "findClusters" initializes a result set, or list of found clusters, to the value NULL, indicating that no clusters have yet been determined. Steps 1606 through 1620 together compose a loop during each iteration of which the routine "findClusters" selects a sequence from the initial set of sequences and attempts to create a cluster starting with that selected sequence. The iteration variable "n" thus ranges, in step 1606, from 0 to N−1. In step 1608, findClusters creates a new cluster that may later be included in the result set and initializes the new cluster to contain the sequence "$S_n$" selected from the initial set of sequences. In step 1610, findClusters computes an initial frequency matrix and an initial information weight matrix corresponding to the new cluster created in step 1608. Steps 1612, 1614, and 1616 represent a nested loop in which findClusters successively adds additional sequences selected from the initial set of sequences "S." In step 1612, findClusters calls the routine "findNxtBest" to find the next sequence to add to the cluster created in step 1608. In step 1614, findClusters determines whether findNxtBest returned a next sequence to add to the cluster. If not, control flows to step 1618. If findNxtBest did return a next sequence, findClusters, in step 1614, determines whether, upon the addition of this next sequence to the cluster, the information content of the information weight matrix calculated for the cluster is still above a threshold value. If so, then, in step 1616, findClusters adds the sequence returned by findNxtBest to the cluster and updates the frequency matrix and the information weight matrix, returning to step 1612 to find yet another sequence to add to the cluster in the next iteration of the nested loop. If the information content of the information matrix instead falls below the threshold value, as determined by findClusters in step 1614, control flows to step 1618. In step 1618, findClusters adds the cluster created in step 1608 to the list of found clusters, if the cluster is not already contained within a cluster in the list of found clusters, and increments the loop variable "n." A first cluster is contained within a second cluster when one half or more of the sequences contained in the first cluster are also contained in the second cluster. In step 1620, findClusters determines whether n is now equal to the number of sequences in the initial set of sequences, N−1. If so, findClusters returns the list of clusters that have been included in the result set in step 1622. Otherwise, control flows to step 1608, where findClusters selects the next sequence from the initial set of sequences and proceeds to attempt to create a new cluster based on that sequence.

Figure 17:
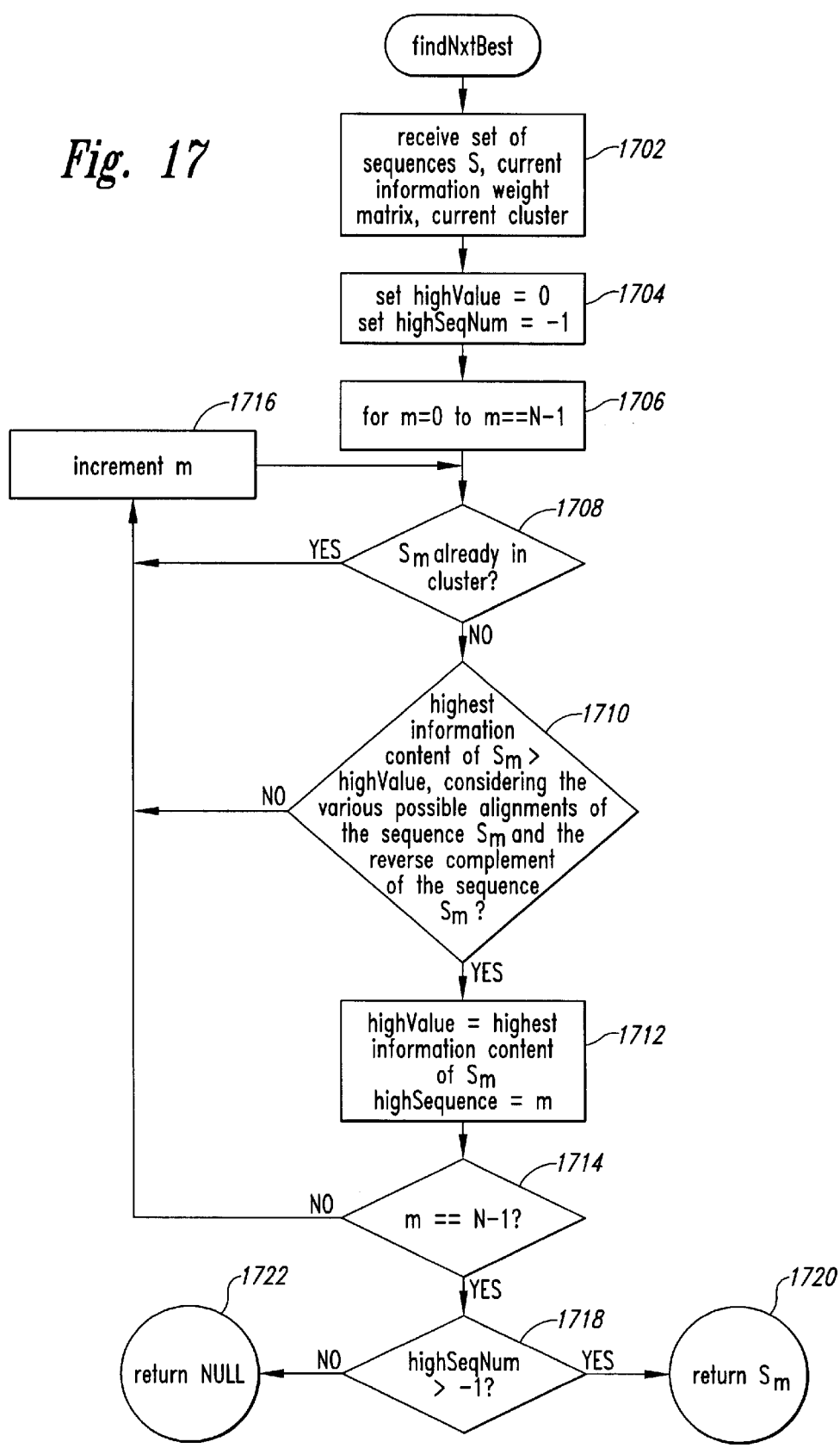
FIG. 17 is a flow-control diagram for the routine "findNxtBest."

FIG. 17 is a flow-control diagram for the routine "findNxtBest." In step 1702, findNxtBest receives a set of initial sequences "S," a current information weight matrix, and a current cluster to which an additional sequence is to be added. In step 1704, findNxtBest initializes a variable "highvalue" to have the value "0" and a variable "highSeqNum" to have the value "1." The variable "highvalue" is used to store the highest information content found for a sequence with respect to the information weight matrix and the variable "highSeqNum" contains the number, or index, of that sequence within the set of sequences "S." Steps 1706 thorough 1716 together compose a loop in which findNxtBest evaluates every sequence within the initial set of sequences to find the next best sequence to add to the cluster. The loop variable "m" ranges in value from 0 to N−1, where N is the number of sequences in S. In step 1708, findNxtBest determines whether the sequence having an index equal to the value of the loop variable "m," i.e. $S_m$, is already contained within the cluster. If so, control flows to step 1716.

Otherwise, findNxtBest computes the information content of $S_m$ in step 1710 and determines whether the information content of this sequence is greater than the current value of the variable "highvalue." If the information content of the selected sequence is not greater than the current value of the variable "highvalue," control flows to step 1716. Otherwise, the sequence $S_m$ has a higher information content than the sequences $S_0$ through $S_{m-1}$ considered in previous iterations of the loop of steps 1706–1716. Therefore, in step 1712, findNxtBest saves the information content of the selected sequence $S_m$ in the variable "highvalue" and saves the index of that sequence, "m," in the variable highSeqNum. In step 1714, findNxtBest decides whether the value of the loop variable "m" currently equals N−1. If so, findNxtBest has considered each sequence within the initial set of sequences "S" and exits the loop to step 1718. If not, control flows to step 1716 where the loop variable "m" is incremented and from which step control flows back to step 1708. In step 1718, findNxtBest determines whether the current value of the variable "highSeqNum" is greater than −1, the initial value to which the variable "highSeqNum" was set in step 1704. If so, findNxtBest has successfully found an additional sequence to add to the current cluster, and returns that sequence in step 1720. Otherwise, no additional sequence has been found, and findNxtBest returns NULL in step 1722.

A pseudocode implementation of the routines "findClusters" and "findNxtBest," diagramed in FIGS. 16 and 17, follows below:

```
1   const int MAX_SEQ;
2   const int WM_THRESHOLD;
3
4   enum bases {A, C, T, G, M};
5   enum seq_sense {original, reverse};
6
7   class sequence
8   {
9      private:
10             seq_sense sense;
11             char* sequence;
12             int num;
13             int shift;
14
15     public:
16             sequence( );
17             ~sequence( );
18             void      reverseComplement( );
19             void      shift (int num);
20             int       getShift( );
21             seq_sense getSense( );
22             int       getNum( );
23             char*     getSequence( );
24  };
25
26  class sequences
27  {
28     private:
29             sequence* seqs;
30             int numSeqs;
31
32     public:
33             sequences( );
34             int getNumSequences( );
35             sequence* getFirstSequence( );
36             sequence* getNextSequence( );
37             sequence* getSequence(int num);
38  };
39
40  class clusteredSequence
41  {
42     private:
43             int num;
```

-continued

```
44          int shift;
45          seq_sense sense;
46
47    public:
48          clusteredSequence(int num, int shift, int sense);
49          int       getNum( );
50          int       getShift( );
51          seq_sense getSense( );
52  };
53
54  class cluster
55  {
56    private:
57          clusteredSequence*   clstr;
58          int                  numSequences;
59
60    public:
61          cluster(clusteredSequence *cseq);
62          ~cluster( );
63          void    add (clusteredSequence *cseq);
64          Bool    containedIn (cluster* potentialParent);
65          Bool    contains (int seqNum);
66          int     getFirst( );
67          int     getNext( );
68          int     getNumSequences( );
69  };
70
71  class clusters
72  {
73    private:
74          cluster*  clstrs;
75          int       numClusters;
76          Bool      internalAdd(cluster* cstr);
77
78    public:
79          clusters( );
80          ~clusters( );
81          void      add(cluster* cstr);
82          int       getNumClusters( );
83          cluster*  getFirstCluster( );
84          cluster*  getNextCluster( );
85  };
86
87  class informationWeightMatrix
88  {
89    private:
90          int fMatrix[M + 1][MAX_SEQ];
91          double wMatrix[M][MAX_SEQ];
92          int num;
93          void computeWeightMatrix( );
94
95    public:
96          informationWeightMatrix( );
97          void    reset(sequence* seq);
98          double  informationContent(sequence* seq);
99          double  addSequence(sequence* seq, cluster* c);
100 }
101
102 Bool    cluster::containedIn (cluster* potentialParent)
103 {
104       int found = 0;
105       double ratio;
106       int nxt;
107
108       nxt = getFirst( );
109       while (nxt >= 0)
110       {
111           if (potentialParent->contains(nxt)) found++;
112           nxt = getNext( );
113       }
114       ratio = found / getNumSequences( );
115       if ratio >= 0.5 return TRUE;
116       else return FALSE;
117 };
118
119 Bool    clusters::add(cluster* potentialAddee)
120 {
121       cluster *c;
122
```

-continued

```
123         if (getNumClusters( ) == 0) return internalAdd(potentialAddee);
124         else
125         {
126             c = getFirstCluster( );
127             while (TRUE)
128             {
129                 if (potentialAddee->containedIn(c)) break;
130                 c = getNextCluster( );
131                 if (c == NULL)
132                 {
133                     return internalAdd(potentialAddee);
134                     break;
135                 }
136             }
137         }
138         return FALSE;
139 }
140
141 void informationWeightMatrix::computeWeightMatrix( )
142 {
143
144         for (int j = 0; j < MAX_SEQ; j++)
145         {
146             for (int k = A; k < M; k++)
147             {
148                 if (fMatrix[M][j] == 0) tmp = log_2 (fMatrix[k][j] / num) + 2;
149                 else if (fMatrix[M][j] == num) tmp = 0
150                 else tmp = log_2((fMatrix[k][j] + fMatrix[4][j] / 4) / num) +
    2;
151                 if (tmp < -14.0) tmp = -14.0;
152                 wMatrix[k][j] = tmp;
153             }
154         }
155 }
156
157 double informationWeightMatrix ::informationContent(sequence* seq)
158 {
159         char *p;
160         double content = 0.0;
161
162         p = seq->getSequence( );
163         for (j = 0; j < MAX_SEQ; j++)
164         {
165             if (*p < M) content += wMatrix[*p++][j]++;
166             else p++;
167         }
168         return content;
169 }
170
171
172 double informationWeightMatrix ::addSequence(sequence* seq, cluster* c)
173 {
174         char *p;
175         double tmp;
176         double content = 0.0;
177         sequence* nxtSeq;
178
179         num++;
180         p = seq->getSequence( );
181         for(int j = 0; j < MAX_SEQ; j++)
182         {
183             fMatrix[*p++][j]++;
184         }
185         computeWeightMatrix( );
186         nxtSeq = c->getFirst( );
187         while (nxtSeq != NULL)
188         {
189             p = nxtSeq->getSequence( );
190             for (j = 0; j < MAX_SEQ;j)
191             {
192                 if (*p < M) content += wMatrix[*p++][j]++;
193                 else p++;
194             }
195             nxtSeq = c->getNext( );
196         }
197         p = seq=>getSequence( );
198         for (j = 0; j < MAX_SEQ; j++)
199         {
200             if (*p < M) content += wMatrix[*p++][j]++;
```

-continued

```
201            else p++;
202        }
203        content = content / num;
204        if (content < WM_THRESHOLD)
205        {
206            p = seq->getSequence( );
207            for (int j = 0; j < MAX_SEQ; j++)
208            {
209                fMatrix[*p++][j]--;
210            }
211            computeWeightMatrix( );
212        }
213        return content;
214 }
215
216 Bool findClusters(sequences & allSeqs, clusters & identifiedClstrs)
217 {
218        sequence* nxt;
219        clusteredSequence* nxtBest;
220        cluster* c;
221        informationWeightMatrix wMatrix;
222        double content;
223
224        nxt = allSeqs.getFirstSequence( );
225        if (nxt == NULL) return FALSE;
226        do
227        {
228            c = new cluster(new clusteredSequence(nxt->getNum( ), nxt-
229                            >getShift( ), nxt->getSense( ));
230            wMatrix.reset (nxt);
231            while (TRUE)
232            {
233                nxtBest = findNextBest(allSeqs, c, wMatrix);
234                if (nxtBest == NULL) break;
235                else
236                {
237                    content = wMatrix.addSequence
238                      (allSeqs.getSequence(nxtBest->getNum( )), c);
239                    if (content < WM_THRESHOLD)
240                    {
241                        delete nxtBest;
242                        break;
243                    }
244                    c->add(nxtBest);
245                }
246            }
247            if (!identifiedClstrs.add(c)) delete c;
248            nxt = allSeqs.getNextSequence( );
249        } until (nxt == NULL);
250 }
251
252 clusteredSequence*     findNxtBest (sequences & allSeqs, cluster* cstr,
253                                    informationWeightMatrix & wMatrix)
254 {
255        sequence *nxt;
256        int shift;
257        double val;
258        double highValue = 0.0;
259        int highSeqNum = -1;
260        seq_sense sense;
261
262        nxt = allSeqs.getFirstSequence( );
263        while (nxt != NULL)
264        {
265            if (cstr->contains(nxt->getNum( ))) continue;
266            for (int k = 0; k < 2; k++)
267            {
268                for (int j = -3; j < 4; j++)
269                {
270                    nxt->shift(j);
271                    val = wMatrix.informationContent(nxt);
272                    if (val > highValue)
273                    {
274                        highValue = val;
275                        sense = nxt->getSense( );
276                        shift = j;
277                        highSeqNum = nxt->getNum( );
278                    }
279                }
```

```
-continued 280            nxt->reverseComplement( );
281        }
282        nxt = allSeqs.getNextSequence( );
283    }
284    if (highSeqNum >= 0) return (new clusteredSequence (highNum, shift,
285    sense));
286    else return NULL;
287 }
```

Two constants are defined in lines 1–2. MAX_SEQ is the maximum number of positions or cells within the character array in which a sequence is stored. WM_THRESHOLD is the threshold value for the information content of the information weight matrix below which additional sequences are not added to a building cluster. Two enumerations are defined in lines 5–6. The enumeration "bases" includes the four single-character designations for nucleotide subunits as well as the letter "M," which indicates a blank position within a sequence. The enumeration "seq_sense" defines the enumerated constants "original" and "reverse" which refer to whether a sequence is in the original form or is in the reverse complement form.

Six classes are declared in lines 7–100. Implementations for the majority of the function members of these classes are not given in this example, both because the implementations may vary widely depending on data structures chosen to store representations of sequences and clusters and because the implementation for these function members is straightforward. Implementations for certain of the function members are provided starting on line 102.

An instance of the class "sequence," declared on lines 7–24, stores a single sequence. The member function "reverseComplement," declared on line 18, causes the sequence to be transformed to its reverse complement, changing the sense of a sequence from "original" to "reverse," or from "reverse" to "original." The function member "shift," declared on line 19, shifts the sequence within the character array in which the sequence is stored a given number of positions to the right or left depending on the size and sign of the argument "num" passed to the member function "shift." The functions "getShift," "getSense," and "getNum," declared on lines 20–22, return the current shift, the current sense, and the number of the sequence within the initial set of sequences. The function "getSequence," declared on line 23, returns a character pointer to the first position of the sequence.

An instance of the class "sequences," declared in lines 26–38, represents the initial set of sequences analyzed by the function "findClusters." The member function "getNumSequences," declared on line 34, returns the number of sequences within the set of sequences represented by an instance of the class "sequences." The member function "getFirstSequence," declared on line 35, returns a pointer to the first sequence within the set of sequences, and the member function "getNextSequence," declared on line 36, returns a pointer to the next sequence in the set of sequences. Member function "getNextSequence" can be called repeatedly to return successive sequences from the set of sequences until member function "getNextSequence" returns a NULL pointer, indicating that no further sequences are contained within the set of sequences. Finally, the member function "getSequence," declared on line 37, returns a pointer to the sequence within the set of sequences indexed by the argument "num." When num has the value "0", for example, member function "getSequence" returns a pointer to the first sequence within the set of sequences.

An instance of the class "clusteredSequence," declared in lines 40–52, represents a single sequence within a cluster of sequences. An instance of this class is, in other words, a place holder for a sequence within a cluster of sequences. An instance of the class "clusteredSequence" is initialized through the constructor declared on line 48. The constructor is supplied with arguments specifying the number of a sequence within an initial set of sequences, the current shift of that sequence, and the current sense of that sequence. Member functions "getNum," "getShift," and "getSense," declared on lines 49–51, return the number of the sequence, the current shift of the sequence, and the sense of the sequence represented by an instance of the class "clusteredSequence."

An instance of the class "cluster," declared on lines 54–69, represents a set of clustered sequences that each, in turn, represents one sequence from an initial set of sequences. An instance of the class "cluster" is initialized by calling the constructor declared on line 61. An initial sequence is provided to the constructor via the argument "cseq." An additional sequence can be added to the cluster by calling the member function "add," declared on line 63. The member function "containedIn," declared on line 64, determines whether another cluster provided by the argument "potentialParent" contains the cluster represented by the instance of the class "cluster." The member function "contains," declared on line 65, determines whether an instance of the class "cluster" contains a particular sequence. The member function "getFirst," declared on line 66, returns the first sequence within a cluster. Additional successive sequences within a cluster are obtained by successive calls to the member function "getNext," declared on line 67. Finally, the member function "getNumSequences," declared on line 68, returns the number of sequences currently contained in the cluster.

The class "clusters," declared on lines 71–85, represents the collection of clusters that are found by the analysis conducted in the routine "findClusters." This class is, in other words, the result set for the analysis. Member functions of the class "clusters," declared on lines 81–84, allow for addition of a cluster into the set of clusters represented by an instance of this class and for the retrieval of clusters contained in the set of clusters represented by an instance of this class.

The class "informationWeightMatrix," declared on lines 87–100, implements the frequency and information weight matrices that are used to model a building cluster, as described above. The member function "computeWeightMatrix," declared on line 93, is used to compute values of the information weight matrix from values stored in the frequency matrix. The member function "reset," declared on line 97, initializes the frequency matrix and the information weight matrix according to an initial sequence supplied by argument "seq." The member function "informationContent," declared on line 98, returns a value that represents the information content of a sequence, supplied as argument "seq," with respect to the current contents of the information weight matrix. The member function "addSequence," declared on line 99, re-computes the frequency matrix and weight matrix following addition of the sequence supplied as argument "seq" to the cluster supplied as argument "c." The member function "addSequence" returns a floating point value indicating the information content of the information weight matrix following addition of the sequence "seq." If, by adding the sequence "seq," the information content of the information weight matrix falls below the threshold value, the frequency matrix and information weight matrix are returned to the state that they had prior to the attempt to add sequence "seq" to cluster "c," thus backing out the addition of the sequence "seq."

Implementations for a number of member functions declared in the above-described classes are given in lines 102–214. An implementation of the function "containedIn" of class "cluster" is given in lines 102–117. Member function "containedIn" iterates through each sequence of the cluster and determines whether that sequence is contained in the potential parent cluster supplied as the argument "potentialParent." If the sequence is contained in the potential parent cluster, variable "found" is incremented on line 111. Member function contained in then computes the ratio of the number of sequences that are found in the potential parent divided by the total number of sequences on line 114. If this ratio is greater than or equal to 0.5, then contained in returns TRUE on line 115. Otherwise, containedIn returns FALSE on line 116. Thus, if one-half or more of the sequences in a cluster also occur in a potential parent cluster, then that cluster is considered to be contained in the potential parent cluster.

An implementation of the member function "add" for the class "cluster" is given on lines 119–139. This member function adds a cluster to the set of clusters that represent the result set for the analysis conducted in the routine "findClusters." If the result set does not already contain any clusters, then the cluster supplied as argument "potentialAddee" is added to the set of clusters on line 123. Otherwise, member function "add" loops through each cluster already contained in the set of clusters represented by an instance of the class "clusters" to determine whether the cluster to be added, "potentialAddee," is contained in any of the clusters already contained in the set of clusters. If the cluster to be added, "potentialAddee," is not contained within any of the clusters, then the cluster to be added, "potentialAddee," is added to the set of clusters on line 133.

An implementation of the member function "computeWeightMatrix" of the class "informationWeightMatrix" is given on lines 141–155. This function computes the values for the information weight matrix according to the set of rules for computing information weight matrix values described above.

An implementation of the member function "informationContent" of class "informationWeightMatrix" is given on lines 157–169. This function implements the calculation of the information content of a sequence provided as argument "seq" with respect to the current values in the information weight matrix, as described above in a mathematical formula.

An implementation of the member function "addSequence" for class "informationWeightMatrix" is given on lines 172–214. This member function computes the frequency matrix and the information weight matrix that reflects addition of the sequence provided by argument "seq" to the cluster provided by argument "c," and returns the resulting information content of the information weight matrix. If, by adding the sequence to the cluster, the information content of the information matrix falls below a threshold value, the frequency matrix and information weight matrix are returned to the state they initially had, prior to the addition of the sequence to the cluster. As implemented in this example, the frequency matrix stores the number of occurrences of each type of nucleotide subunit within the sequences in a cluster rather than the frequency of occurrence of the nucleotide subunit. The frequencies are calculated during the process of computing values for the information weight matrix. In lines 180–184, member function addsequence loops through the subunits of the sequence "seq" and increments values in the frequency matrix that correspond to the nucleotide subunits at each position within the sequence. Then, on line 185, member function "addSequence" computes the information weight matrix from the values stored in the frequency matrix. In lines 186–203, addsequence computes the information content of the resulting information weight matrix according to the mathematical formula given above. If the information content is less than the threshold value, as determined on line 204, member function "addSequence" returns the values of the frequency matrix to the values that the frequency matrix had at the start of execution of the member function and re-computes the information weight matrix values to restore the values of the information weight matrix to the values that the information weight matrix had prior to execution of member function "addSequence." Finally, on line 213, member function "addSequence" returns the information content of the information weight matrix based on addition of the sequence "seq" to cluster "c."

An implementation of the routine "findClusters", diagramed in FIG. 17, is given on lines 216–250. In the loop comprising lines 226–249, findClusters analyzes, in turn, each sequence from an initial set of sequences supplied as argument "allSeqs." First, on line 228, findClusters creates a new cluster initialized with the selected sequence. Then, in the inner loop comprising lines 231–246, findClusters continually calls the routine "findNxtBest" in order to find the next best sequence to add to the cluster. If no further sequences are found by the routine "findNxtBest," findClusters breaks out of the inner loop on line 234. Otherwise, findClusters attempts to add the found sequence to the cluster in lines 237–238. If the information content of the information weight matrix falls below the threshold value, as detected on line 239, then the found sequence is not added to the cluster and findClusters breaks out of the inner loop on line 242. Otherwise, findClusters adds the next sequence to the cluster on line 244. On line 247, following completion of the inner loop comprising lines 231–246, findClusters attempts to add the new cluster created on line 228 to the result set "identifiedClstrs." As discussed above, this new cluster is added only if it does not already occur within the result set "identifiedClstrs."

An implementation of the routine "findNxtBest," diagramed in FIG. 18, is given on lines 252–286. The routine "findNxtBest" looks through all of the sequences in the initial set of sequences supplied as argument "allSeqs" to determine a next best sequence from the set of sequences to add to the building cluster supplied as argument "cstr" and modeled by the information weight matrix supplied as argument "wMatrix." In the loop comprising lines 263–283, findNxtBest considers each sequence within the list of sequences "allSeqs." If a selected sequence is already contained within the building cluster, as detected on line 265, then it is ignored. In the nested loop comprising lines 266–281, findNxtBest tries various possible alignments of the selected sequence and various possible alignments of the reverse complement of the selected sequence and, if the information content of a particular alignment and a particular sense of the selected sequence exceeds the highest value so far detected for any selected sequence, then the information content, sense, shift, and number of the selected sequence are saved in local variables. When all of the sequences have been considered, then, if another sequence has been found for addition to the cluster "cstr," an indication of that sequence is returned on line 284. Otherwise, findNxtBest returns a value NULL to indicate that no further sequences can be found to add to the cluster.

Although the present invention has been described in terms of one embodiment, it is not intended to be limited to this embodiment. Modifications within the spirit of the invention would be apparent to those skilled in the art. For example, as mentioned above, the present invention might be employed to look for similar sub-sequences of amino acid subunits within a set of amino acid sequences corresponding to different polypeptide polymers. Such sub-sequences might represent conserved structural regions within a family of proteins and might be useful for identifying catalytic sites, receptor binding sites, or other functional regions within the family of proteins. Applications of the present invention are not limited to the analysis of bio-polymers, but may include such diverse areas as linguistics, image processing, and other pattern recognition tasks. For example, the present invention might be applied to recognize roots within the words that together compose the vocabulary of a particular language. Alternatively, the present invention might be employed to identify common patterns within character string or bit map representations of graphical images. In all of these cases, the present invention would require modification of the frequency matrix and the information weight matrix to include a number of rows corresponding to the number of possible components of the sequences to be analyzed and to include a number of columns corresponding to somewhat more than the total number of components that compose a typical sequence. Various obvious alternate forms of the information weight matrix may be employed, including using a different floor value for information weight matrix terms rather than −14, and using different weighting factors, constant multipliers, and calculation formulas that preserve the relative information content rankings of sequences. The scope of the present invention is defined by the claims that follow:

What is claimed is:

1. A method embodied in a computer program that executes on a computer for identifying new clusters of biopolymer sequences from an initial set of biopolymer sequences, each new cluster of biopolymer sequences comprising a number of similar biopolymer sequences selected from the initial set of biopolymer sequences, the method comprising:

iteratively identifying a next new cluster from the initial set of biopolymer sequences by, selecting a next biopolymer sequence from the initial set of biopolymer sequences to be the single biopolymer sequence in a potential next new cluster;

calculating a current information weight matrix for the potential next new cluster containing the selected next biopolymer sequence;

successively choosing a next biopolymer sequence from the initial set of biopolymer sequences to add to the potential next new cluster by, choosing a next biopolymer sequence from the initial set of biopolymer sequences having the highest information content with respect to the current information weight matrix for the potential next new cluster, the chosen next biopolymer sequence not already included in the potential next new cluster; and adding the chosen next biopolymer sequence to the potential next new cluster and re-calculating the current information weight matrix for the potential next new cluster when the information content of the potential next new cluster with respect to the re-calculated current information weight matrix is not less than a threshold information content;

until no biopolymer sequence can be chosen from the initial set of biopolymer sequences that is not already included in the potential next new cluster and that can be added to the potential next new cluster without causing the information content of the potential next new cluster with respect to the current information weight matrix to fall below a threshold information content; and comparing the potential next new cluster to all previously identified clusters and, when the potential next new cluster is not contained in any of the previously identified clusters, identifying the potential next new cluster as a next new cluster and reporting the identified next new cluster.

2. The method of claim 1 wherein the biopolymer sequences in the initial set of biopolymer sequences are linear sequences of subunits, each subunit of the biopolymer sequence having a unique position within the linear sequence of subunits that compose the biopolymer sequence, the subunits of a biopolymer sequence selected from a set of allowable subunits, each allowable subunit associated with a unique ordinal value corresponding to the order of the allowable subunit within the set of allowable subunits.

3. The method of claim 2 wherein the subunits are characters in an array of characters within a computer readable memory.

4. The method of claim 2 wherein a biopolymer sub-sequence is a sequence of subunits contained within a biopolymer sequence.

5. The method of claim 4 wherein the common biopolymer sub-sequence contained in each biopolymer sequence within a cluster may vary in sequence and in alignment with respect to the different biopolymer sequences of the cluster.

6. The method of claim 2 wherein the subunits represent nucleotides within a sequence selected from among a DNA sequence and an RNA sequence.

7. The method of claim 2 wherein the subunits represent amino acid subunits of a polypeptide polymer.

8. The method of claim 2 wherein the subunits that comprise a biopolymer sequence are computationally represented so that the starting position of the biopolymer sequence may be shifted one position rightward by adding a blank subunit to the left end of the biopolymer sequence and renumbering the subunits of the biopolymer sequence starting with the added blank subunit and so that the bipolymer sequence may be shifted one position leftward by removing a blank subunit from the left end of the biopolymer sequence and renumbering the subunits of the biopolymer sequence starting with the subunit that followed the removed blank subunit, a blank subunit included as one of the allowable subunits in the set of allowable subunits and associated with a unique ordinal value.

9. The method of claim 8 wherein the starting position of the biopolymer sequence may be shifted multiple positions either in a rightward or leftward direction.

10. The method of claim 8 wherein during the first iteration of identifying a next new cluster, the biopolymer sequence selected in the step of selecting a biopolmer sequence from the initial set of biopolymer sequences to be the first biopolymer sequence of a potential next new cluster is the first biopolymer sequence of the initial set of biopolymer sequences, and wherein successive biopolymer sequences from the initial set of biopolymer sequences are selected in each successive iteration of the step of selecting a biopolymer sequence from the initial set of biopolymer sequences to be the first biopolymer sequence of a potential next new cluster.

11. The method of claim 8 wherein the current information weight matrix re-calculated for a cluster following the addition of each biopolymer sequence to the cluster contains rows and columns of values, each value indexed by a number of the row and a number of the column in which the value occurs in the information weight matrix.

12. The system of claim 11 wherein the information weight matrix is computed from a frequency matrix having rows and columns of values, each value of the frequency matrix indexed by a number of the row and a number of the column in which the value occurs in the information weight matrix.

13. The method of claim 12 wherein the value in the frequency matrix located in row j and in column k corresponds to the frequency that the subunit associated with unique ordinal value j occurs in a k-th position within the biopolymer sequences of the cluster.

14. The method of claim 13 wherein the value of the information weight matrix at row j and column k is computed by a set of rules that follow:

if the value of the frequency matrix in the row indexed by the unique ordinal value associated with the blank subunit and in column k corresponds to a frequency of 1.0, then the value in the information weight matrix at row j and column k is 0.0;

if the value of the frequency matrix in the row indexed by the unique ordinal value associated with the blank subunit and in column k corresponds to a frequency of 0.0, then the value of information weight matrix at row j and column k is 2 plus the log, to base 2, of the frequency corresponding to the value of the frequency matrix at row j and column k;

if the value of the frequency matrix in the row indexed by the unique ordinal value associated with the blank subunit and in column k corresponds to a frequency between 0.0 and 1.0, then the value of information weight matrix at row j and column k is 2 plus the log, to base 2, of the frequency corresponding to the value of frequency matrix at row j and column k plus the frequency corresponding to the value of frequency matrix in the row indexed by the unique ordinal value associated with the blank subunit and in column k divided by 4; and if any value for the information weight matrix computed by these rules is less than a minimum value, that value is set to the minimum value.

15. The method of claim 14 wherein the minimum value is −14.0.

16. The method of claim 14 wherein the information content of a biopolymer sequence with respect to the potential next new cluster is the sum of those values of the current information weight matrix calculated for the potential next new cluster that correspond to the subunits within the biopolymer sequence, wherein a value in the current information weight matrix in row j and in column k corresponds to a subunit within the biopolymer sequence at position k and associated with the unique ordinal value j.

17. The method of claim 16 wherein the information content of the current information weight matrix is an average value of information contents of the biopolymer sequences within the cluster for which the current information weight matrix was calculated.

18. The method of claim 17 wherein a first cluster is contained within a second cluster when at least one half of the biopolymer sequences included in the first cluster are also contained within the second cluster.

19. The method of claim 8 wherein in the step of choosing a next bipolymer sequence from the initial set of biopolymer sequences having the highest information content with respect to the potential next new cluster, the chosen next biopolymer sequence is shifted a number of times rightward and a number of times leftward in order that an alignment giving the highest information content with respect to the current information weight matrix for the potential next cluster is chosen as the alignment for the chosen next biopolymer sequence.

20. The method of claim 8 wherein, in the step of choosing a next biopolymer sequence from the initial set of biopolymer sequences having the highest information content with respect to the potential next new cluster, the chosen next biopolymer sequence is transformed by a set of transformation rules in order that a transformation state giving the highest information content with respect to the current information weight matrix for the potential next cluster is chosen as the transformation state for the chosen next biopolymer sequence.

21. A system for identifying new biopolymer sequence clusters from an initial set of biopolymer sequences each new biopolymer sequence cluster comprising a number of similar biopolymer sequences, selected from the initial set of biopolymer sequences, the system comprising:

an input device that receives the initial set of biopolymer sequences;

a memory that stores the initial set of biopolymer sequences, a result set of biopolymer sequence clusters, a current information weight matrix, and a current biopolymer sequence cluster; and a processor that
   transfers the initial set of biopolymer sequences received by the input device to the memory;
   selects each biopolymer sequence from the initial set of biopolymer sequences stored in memory; and
   for each selected biopolymer sequence,
      creates in memory a potential new biopolymer sequence cluster that contains the single selected biopolymer sequence;
      computes an information weight matrix for the potential new biopolymer sequence cluster that contains the selected biopolymer sequence;
      successively chooses a next biopolymer sequence from the initial set of biopolymer sequences not already included in the new biopolymer sequence cluster to add to the potential new biopolymer sequence cluster;
      for each next biopolymer sequence,
         recomputes the information weight matrix for the potential new biopolmer sequence cluster including the next biopolymer sequence,
         computes an information content of the recomputed information weight matrix, and
         adds the next biopolymer sequence to the potential new biopolymer sequence cluster,
      until the computed information content of the recomputed information weight matrix falls below a threshold value; and
   when the computed information of the information weight matrix content falls below a threshold value and when the potential new biopolymer sequence cluster is not contained within any biopolymer sequence cluster already contained in the result set, adds the potential new biopolymer sequence cluster to the result set.

22. The system of claim 1 wherein the biopolymer sequences in the initial set of biopolymer sequences are linear sequences of characters, a character represented by a group of contiguous bits within the memory, the characters that can be used to compose a biopolymer sequence defined by a set of allowable biopolymer sequence characters, each character of the biopolymer sequence having a unique position within the linear sequence of characters that compose the biopolymer sequence.

23. The system of claim 22 wherein the characters represent nucleotides within a sequence selected from among DNA and RNA sequences.

24. The system of claim 22 wherein the characters represent amino acid subunits in a polypeptide polymer.

25. The system of claim 22 wherein a biopolymer sub-sequence is a sequence of characters contained within a biopolymer sequence.

26. The system of claim 25 wherein the common biopolymer sub-sequence shared by biopolymer sequences within a biopolymer sequence cluster may vary in sequence and in alignment within the different biopolymer sequences of the biopolymer sequence cluster.

27. The system of claim 22 wherein a frequency matrix having rows and columns of values, each value indexed by a number of the row and a number of the column in which it occurs, is computed for a biopolymer sequence cluster prior to computation of the information weight matrix, a value in the frequency matrix located in row j and in column k corresponding to the frequency that a j-th character of the set of allowable characters occurs in a k-th position within the biopolymer sequences of the biopolymer sequence cluster, the values of the frequency matrix ranging from 0.0 to 1.0 corresponding to from 0% occurrence to 100% occurrence.

28. The system of claim 27 wherein the frequency matrix includes a special row, a value in the special row and in the k-th column corresponding to the frequency that a k-th position within the biopolymer sequences of the biopolymer sequence cluster does not contain a character from the set of allowable biopolymer sequence characters.

29. The system of claim 28 wherein the information weight matrix has rows and columns of values, each value indexed by a number of the row and a number of the column in which it occurs, the value of the information weight matrix in row j and in column k computed by a set of rules which follow:
   if the value of the frequency matrix in the special row at column k is 1.0, then the value of information weight matrix in row j and in column k is 0.0;
   if the value of the frequency matrix in the special row and in column k is 0.0, then the value of information weight matrix in row j and in column k is 2 plus the log, to base 2, of the value of frequency matrix in row j and in column k;
   if the value of the frequency matrix in the special row at column k is between 0.0 and 1.0, then the value of the information weight matrix in row j and in column k is 2 plus the log, to base 2, of the value of frequency matrix in row j and in column k plus the value of frequency matrix in the special row and in column k divided by 4; and
   if any value for the information weight matrix computed by these rules is less than a minimum value, that value is set to the minimum value.

30. The system of claim 29 wherein the minimum value is −14.0.

31. The system of claim 22 wherein a frequency matrix having rows and columns of values, each value indexed by a number of the row and a number of the column in which the value occurs, is computed for a biopolymer sequence cluster prior to computation of the information weight matrix, a value in the frequency matrix located in row j and in column k corresponding to a number of times that a j-th character of the set of allowable characters appears in the k-th position within the biopolymer sequences of the biopolymer sequence cluster, the values of the frequency matrix ranging from 0 to the number of biopolymer sequences in the biopolymer sequence cluster.

32. The system of claim 31 wherein the frequency matrix includes a special row, a value in the special row and in the k-th column corresponding to the number of biopolymer sequences in the biopolymer sequence cluster in which the k-th position does not contain a character from the set of allowable biopolymer sequence characters.

33. The system of claim 32 wherein the information weight matrix has rows and columns of values, each value indexed by a number of the row and a number of the column in which it occurs, the value of the information weight matrix in row j and in column k computed by a set of rules that follow:

- if the value of the frequency matrix in the special row and in column k is 1.0, then the value of information weight matrix in row j and in column k is 0.0;
- if the value of the frequency matrix in the special row in column k is 0.0, then the value of information weight matrix in row j and in column k is 2 plus the log, to base 2, of the value of frequency matrix in row j and in column k divided by the number of biopolymer sequences in the biopolymer sequence cluster;
- if the value of the frequency matrix in the special row and in column k is between 0.0 and 1.0, then the value of information weight matrix in row j and in column k is 2 plus the log, to base 2, of the value of frequency matrix in row j and in column k divided by the number of biopolymer sequences in the biopolymer sequence cluster plus the value of frequency matrix in the special row and in column k divided by 4 times the number of biopolymer sequences in the biopolymer sequence cluster; and
- if any value for the information weight matrix computed by these rules is less than a minimum value, that value is set to the minimum value.

34. The system of claim 21 wherein the step of successively choosing a next biopolymer sequence from the initial set of biopolymer sequences to add to the potential new biopolymer sequence cluster further includes:

selecting a biopolymer sequence from the initial set of biopolymer sequences that is not already contained in the potential new biopolymer sequence cluster and that has a highest information content of all the biopolymer sequences of the initial set of biopolymer sequences that are not already contained in the potential new biopolymer sequence cluster with respect to the current values of the information weight matrix, the selected biopolymer sequence aligned to maximize the information content.

35. The system of claim 34 wherein the selected biopolymer sequence is transformed to maximize the information content.

36. The system of claim 21 wherein the result set is a list of biopolymer sequence cluster data structures.

37. The system of claim 21 wherein a biopolymer sequence cluster is a computer-readable data structure that contains indications of the biopolymer sequences included in the biopolymer sequence cluster and that, for each biopolymer sequence contained in the cluster, contains an indication of an alignment shift that has been applied to the biopolymer sequence in order that the common sub-biopolymer sequence included in the biopolymer sequence corresponds closely to the common sub-biopolymer sequence in the other biopolymer sequences of the biopolymer sequence cluster in starting position.

38. The system of claim 37 wherein the biopolymer sequence cluster data structure also contains, for each biopolymer sequence contained in the cluster, an indication of a sequence transformation that has been applied to the biopolymer sequence in order that the common sub-biopolymer sequence included in the biopolymer sequence corresponds closely to the common sub-biopolymer sequences in other biopolymer sequences of the biopolymer sequence cluster with regard to sequence.

39. The method of claim 1 wherein reporting the identified next new cluster further comprises entering a computer-encoded designation of the identified next new cluster into a result set stored within the computer.

40. The method of claim 1 wherein reporting the identified next new cluster further comprises sending a computer-encoded designation of the identified next new cluster to a remote computer or remote computer storage medium.

41. The method of claim 1 wherein reporting the identified next new cluster further comprises displaying an indication of the identified next new cluster on a display device connected to the computer.

* * * * *